(12) United States Patent
Yallop

(10) Patent No.: US 7,291,484 B2
(45) Date of Patent: Nov. 6, 2007

(54) PROCESSES FOR CULTURING E1-IMMORTALIZED CELLS TO INCREASE PRODUCT YIELDS

(75) Inventor: Christopher A. Yallop, Wassenaar (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 11/259,245

(22) Filed: Oct. 26, 2005

(65) Prior Publication Data

US 2006/0240513 A1 Oct. 26, 2006

Related U.S. Application Data

(63) Continuation of application No. PCT/EP2004/050724, filed on May 6, 2004.

(30) Foreign Application Priority Data

| May 9, 2003 | (WO) | PCT/EP03/50155 |
| Sep. 1, 2003 | (WO) | PCT/EP03/50390 |
| Dec. 4, 2003 | (WO) | PCT/EP03/50940 |
| Jan. 30, 2004 | (WO) | PCT/EP04/50061 |

(51) Int. Cl.
C12P 23/00 (2006.01)
C12P 21/08 (2006.01)
C12N 15/00 (2006.01)
C12N 5/02 (2006.01)
C12N 5/06 (2006.01)

(52) U.S. Cl. ............ 435/69.1; 435/70.3; 435/375; 435/383; 435/455

(58) Field of Classification Search .......... None
See application file for complete search history.

(56) References Cited

U.S. PATENT DOCUMENTS

| 4,703,008 A | 10/1987 | Lin |
| 4,835,260 A | 5/1989 | Shoemaker |
| 5,047,335 A | 9/1991 | Paulson et al. |
| 5,192,539 A | 3/1993 | Van Der Marel et al. |
| 5,441,868 A | 8/1995 | Lin |
| 5,457,089 A | 10/1995 | Fibi et al. |
| 5,494,790 A | 2/1996 | Sasaki et al. |
| 5,631,158 A | 5/1997 | Dorai et al. |
| 5,767,078 A | 6/1998 | Johnson et al. |
| 5,773,569 A | 6/1998 | Wrighton et al. |
| 5,789,247 A | 8/1998 | Ballay et al. |
| 5,830,851 A | 11/1998 | Wrighton et al. |
| 5,835,382 A | 11/1998 | Wilson et al. |
| 5,856,292 A | 1/1999 | Thomas et al. |
| 5,856,298 A | 1/1999 | Strickland |
| 5,994,128 A | 11/1999 | Fallaux et al. |
| 6,033,908 A | 3/2000 | Bout et al. |
| 6,395,519 B1 | 5/2002 | Fallaux et al. |
| 6,413,746 B1 | 7/2002 | Field |
| 6,475,753 B1 | 11/2002 | Ruben et al. |
| 6,492,169 B1 | 12/2002 | Vogels et al. |
| 6,506,598 B1 | 1/2003 | Andersen et al. |
| 6,558,948 B1 | 5/2003 | Kochanek et al. |
| 6,653,101 B1 | 11/2003 | Cockett et al. |
| 6,855,544 B1 | 2/2005 | Hateboer et al. |
| 6,878,549 B1 | 4/2005 | Vogels et al. |
| 2002/0116723 A1 | 8/2002 | Grigliatti et al. |
| 2003/0087372 A1* | 5/2003 | DelaCruz et al. .......... 435/69.1 |
| 2003/0087437 A1 | 5/2003 | Asada et al. |
| 2003/0092160 A1 | 5/2003 | Bout et al. |

FOREIGN PATENT DOCUMENTS

| EP | 0 185 573 | 6/1986 |
| EP | 0 411 678 | 2/1991 |
| EP | 0 833 934 B1 | 4/1998 |
| EP | 1 108 787 A2 | 6/2001 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 97/18318 | 5/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 A2 | 10/2000 |
| WO | WO 01/05945 A2 | 1/2001 |
| WO | WO 01/38362 A2 | 5/2001 |
| WO | WO 02/18948 | 3/2002 |
| WO | WO 02/053580 | 7/2002 |
| WO | WO 03/003810 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |
| WO | WO 2004/099396 A1 | 11/2004 |

OTHER PUBLICATIONS

Kurokawa, et al Biotech. Bioeng. 1994. vol. 44, pp. 95-103.*

(Continued)

*Primary Examiner*—Celine Qian
*Assistant Examiner*—Laura M Mitchell
(74) *Attorney, Agent, or Firm*—TraskBritt, P.C.

(57) ABSTRACT

The invention provides processes for culturing cells derived from embryonic retinoblast cells immortalized by adenovirus E1 sequences, preferably PER.C6® (human embryonic retina) cells, to improve product yields from such cells. Feed strategies for such cells and cultures with very high cell densities are provided, resulting in high yields of products, such as recombinant antibodies.

24 Claims, 12 Drawing Sheets

OTHER PUBLICATIONS

Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, BioTechniques 1993, pp. 972-978, vol. 14, No. 6.

Bout et al., "Improved helper cells for RCA-free production of El-deleted recombinant adenovirus vectors," Cancer Gene Therapy, 1996, pp. S24, vol. 3, No. 6.

Bout et al., "Production of RCA-free batches of El-deleted recombinant adenoviral vectors on PER.C6," Nucleic Acids Symp. Ser. 1998, XP-002115716, pp. 35-36.

Boutl et al., A novel packaging cell line (PER.C6) for efficient production of RCA-free batches of El-deleted recombinant adenoviral vectors, Cancer Gene Therapy, 1997, pp. S32-S33, vol. 4, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.

Carroll et al., Abstract, Differential Infection of Receptor-modified Host Cells by Receptor-Specific Influenza Viruses, Virus Research, Sep. 1985, pp. 165-179, vol. 3, No. 2.

Certificate of deposit of the PER.C6 cell line (ECACC deposit under No. 96022940).

Ciccarone et al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

Cronan, Abstract, Biotination of Proteins in-vivo a post-translational modification to label purify and study proteins, Journal of Biological Chemistry, Jun. 25, 1990, pp. 10327-10333, vol. 265, No. 18.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithetial Cells Derived from Adenoids, Journal of Virology, Mar. 1996, pp. 2055-2058, vol. 70, No. 3.

Fallaux et al, "New helper cells and matched early region I-deleted adenovirus vectors prevent generation of replication-competent adenoviruses," Human Gene Therapy, Sep. 1, 1998, vol. 9, No. 1, pp. 1909-1917. Abstract.

Fallaux et al., Characterization of 911: A New Helper Cell Line for the Titration and Propagation of Early Region I-Deleted Adenoviral Vectors, Human Gene Therapy, Jan. 20, 1996, pp. 215-222, vol. 7.

Gallimore et al., Transformation of Human Embryo Retinoblasts with Simian Virus 40, Adenovirus and ras Oncogenes, Anticancer Research, 1986, pp. 499-508, vol. 6.

Garnier et al., Scale-up of the adenovirus expression system for the production of recombinant protein in human 293S cells, Cytotechnology, 1994, pp. 145-155, vol. 15.

GenBank Accession No. X02996.1, 1993, "Adenovirus type 5 left 32% of the genome."

Ghosh-Choudhury et al., Protein IX, a minor component of the human adenovirus capsid, is essential for the packaging of the full length genomes, The EMBO Journal, 1987, pp. 1733-1739, vol. 6, No. 6.

GIBCO cell culture, A Guide to Serum-Free Cell Culture, www.invitrogen.com.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached tot he Gal(beta-1-4)GlcNA(beta-1-2)Man(alpha-1-3)-branch of diantennary oligosaccharides from secreted recombinant beta-trace protein, Eur. J. Biochem, 1995, pp. 715-725, vol. 232, No. 3, Berlin, Germany.

Graham et al., "Characteristics of a Human Cell Line Transformed by DNA from Human Adenovirus Type 5," J. Gen. Virol., 1997, pp. 59-72, vol. 36.

Graham et al., "Growth of 293 cells in suspension culture," J Gen Virol, Mar. 1987, pp. 937-940, vol. 68.

Graham, Cell Lines, Promochem (visited Apr. 10, 2005) <http://www.tgepromochem-atcc.com/SearchCatalogs/longview.cfm?view=ce, 1146678...>.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region I-transformed human cells do not cause up-regulation of MDM2 expression," Virology, 1995, vol. 210, No. 2, pp. 323-334. Abstract.

Hollister et al., Stable expression of mammalian betaI,4-galactosyltransferase extends the N-glycosylation pathway in insect cells, Glycobiology, 1998, pp. 473-480, vol. 8, No. 5, IRL Press, United Kingdom.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.

Paul et al., Increased Viral Titer Through Concentration of Viral Harvests from Retroviral Packaging Lines, Human Gene Therapy, 1993, pp. 609-615, vol. 4.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez.query/fcgi?CMD=search&DB=pubmed.

Reina et al., Comparison of Madin-Darby Canine Kidney cells ( MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Schiedner et al., Abstract, Efficient transformation of primary human amniocytes by El functions of Ad5: generation of new cell lines for adenoviral vector production, 2000, Hum. Gene Ther. 11, 2105-2116.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoproteins Is Not Required for Nuclear Accumulation or the Expression and Replication of a Model RNA," Journal of Virology, Jun. 1998, pp. 5307-5312, vol. 72, No. 6.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

Yallop et al., "PER.C6® Cells for the Manufacture of Biopharmaceutical Proteins," Modern Biopharmaceuticals, ED. J. Knablein, 2005, WILEY-VCH Verlag GmbH & Co. KGaA, Weinheim, Germany.

PCT International Search Report, PCT/EP2004/050724, dated Oct. 1, 2004.

PCT International Preliminary Report, PCT/EP2004/050724, dated Jan. 27, 2005.

Bout et al., "PER.C6 as production platform for human monoclonal antibodies," Human Antibodies, Oct. 8, 2003, pp. 30, vol. 12, No. 1-2.

Jones et al., "High-Level Expression of Recombinant IgG in the Human Cell Line PER.C6," Biotechnology Progress, Jan. 14, 2003, pp. 163-168, vol. 19.

Jones et al., "PER.C6 Cell LIne for Human Antibody Production: Crucell's Technology Maintains 'Human' Glycoylation Patterns," Genetic Engineering News, May 15, 2002, pp. 50, 54, vol. 80, No. 5.

Xie et al., "Serum-Free Suspension Cultivation of PER.C6 Cells and Recombinant Adenovirus Production Under Different pH Conditions," Biotechnology and Bioengineering, Dec. 5, 2002, pp. 569-579, vol. 80, No. 5.

Xie et al., "Large-Scale Propagation of a Replication-Defective Adenovirus Vector in Stirred-Tank Bioreactor PER.C6 Cell Culture Under Sparging Conditions," Jul. 5, 2003, Biotechnology and Bioengineering, pp. 45-52, vol. 83, No. 1.

Pham et al., "Large-Scale Transient Transfection of Serum-Free Suspension-Growing HEK293 EBNA1 Cells: Peptone Additives Improve Cell Growth and Transfection Efficiency," Biotechnology and Bioengineering, Nov. 5, 2003, pp. 332-342, vol. 84, No. 3.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Yan et al., Novel Asn-linked oligosaccharides terminating in GalNAcAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yeager et al., Constructing immortalized human cell lines, Current Opinion Biotechnology, 1999, pp. 465-469, vol. 10.

Yeh et al., Adenoviral Vectors, pp. 25-42 of "Concepts in Gene Therapy," Publisher: Walter de Gruyter, New York, 1997.

Yu et al., "Enhanced c-erbB-2/neu expression in human overian cancer cells correlates with more severe malignancy that can be suppressed by E1A," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

NCBI Entrez Nucleotide accession No. U38242, 1995.

NCBI Entrez Nucleotide accession No. X02996 J01967 J01968 J01970 J01971 J01972 J01974 J01976 J01977 J01978 J01979 K00515 V00025 V00026 V00027 V00029, 1992.

Neumann et al., "Generation of influenza A viruses entirely from cloned cDNAs," Proc. Natl. Acad. Sci., Aug. 1999, pp. 9345-9350, vol. 96.

Notice of Opposition of a European Patent for 1 161 548 by Serono, 2005.

Opposition against European patent 1 108 878 B1 filed Oct. 5, 2005 in the name and on behalf of CEVEC Phannaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Pau et al., Abstract, The human cell line PER.C6 provides a new manufacturing system for the production of influenza vaccines, Vaccine, Mar. 21, 2001, pp. 2716-2721, vol. 19, No. 17-19.

Interlocutory Decision of the Opposition Division of Jul. 21, 2003 in the case EP 0 695 351(European application 94 913 174.2).

Jenkins et al., Getting the glycosylation right: Implications for the biotechnology industry, Nature Biotechnology, Aug. 1996, pp. 975-981, vol. 14, No. 8, Nature Publishing, US.

Lopez et al., Efficient production of biologically active human recombinant proteins in human lymphoblastoid cells form integrative and episomal expression vectors, Gene, 1994, pp. 285-291, vol. 148.

Louis et al., Cloning and Sequencing of the Cellular—Viral Junctions from the Human Adenovirus Type 5 Transformed 293 Cell Line, Virology, 1997, pp. 423-429, vol. 233.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type I Lethal and Latent Infections by Secreted Recombinant Glycoprotein B Constitutively Expression in Human Cells with a BK Virus Episomal Vector," Journal of Virology, Jan. 1990, pp. 431-436, vol. 64, No. 1.

Marketing Authorization and Scientific Discussion for Xigris, 2002.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

NCBI Entrez Nucleotide accession No. NC_002018.

\* cited by examiner

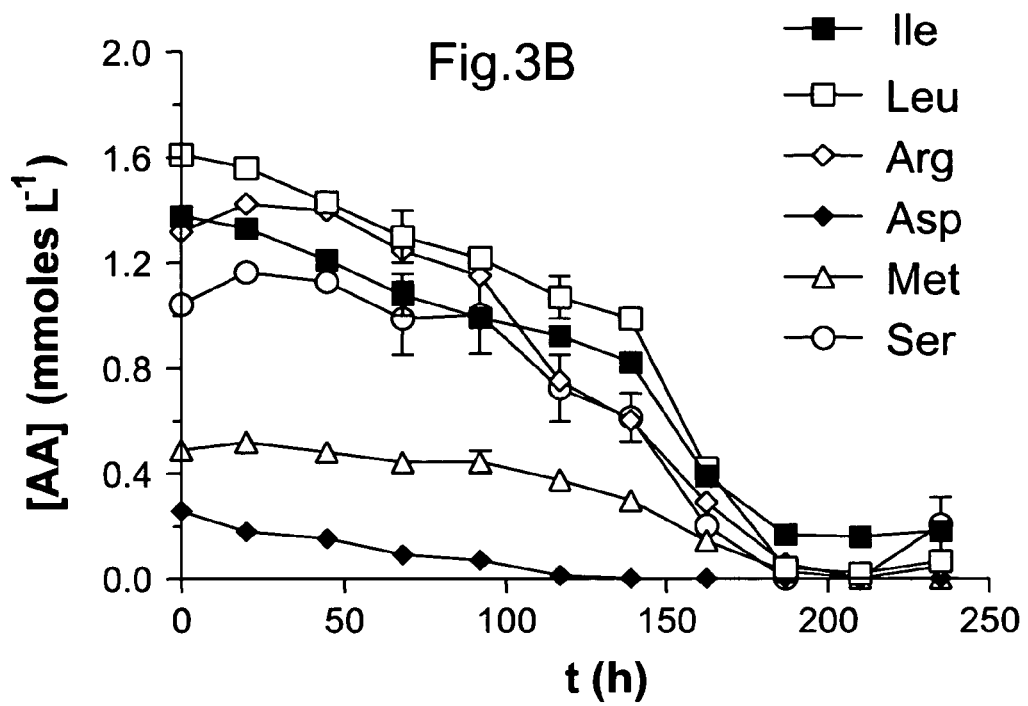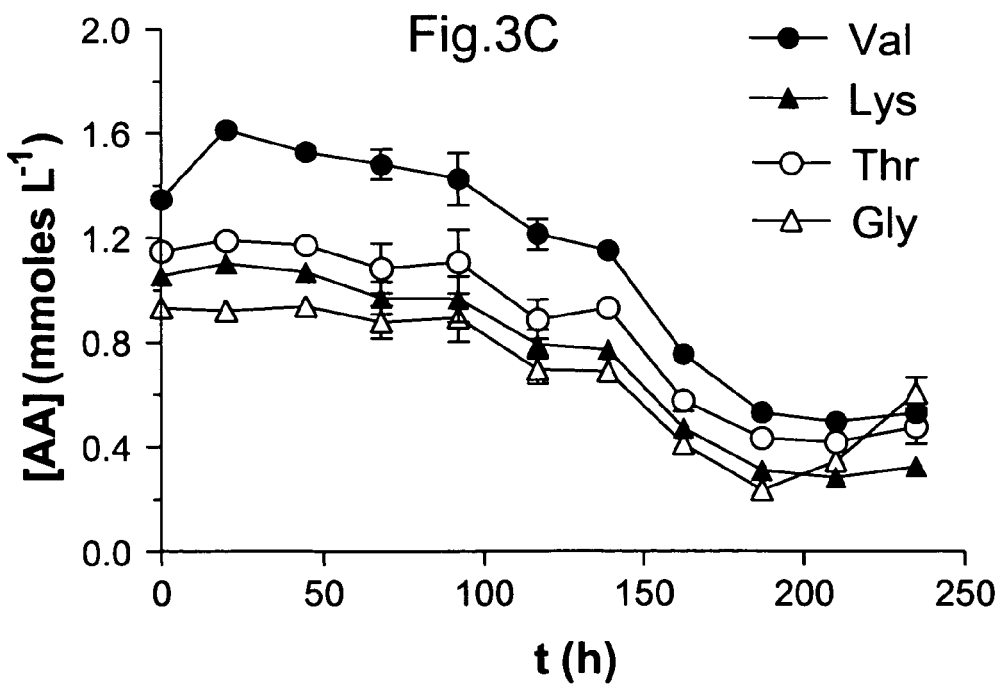

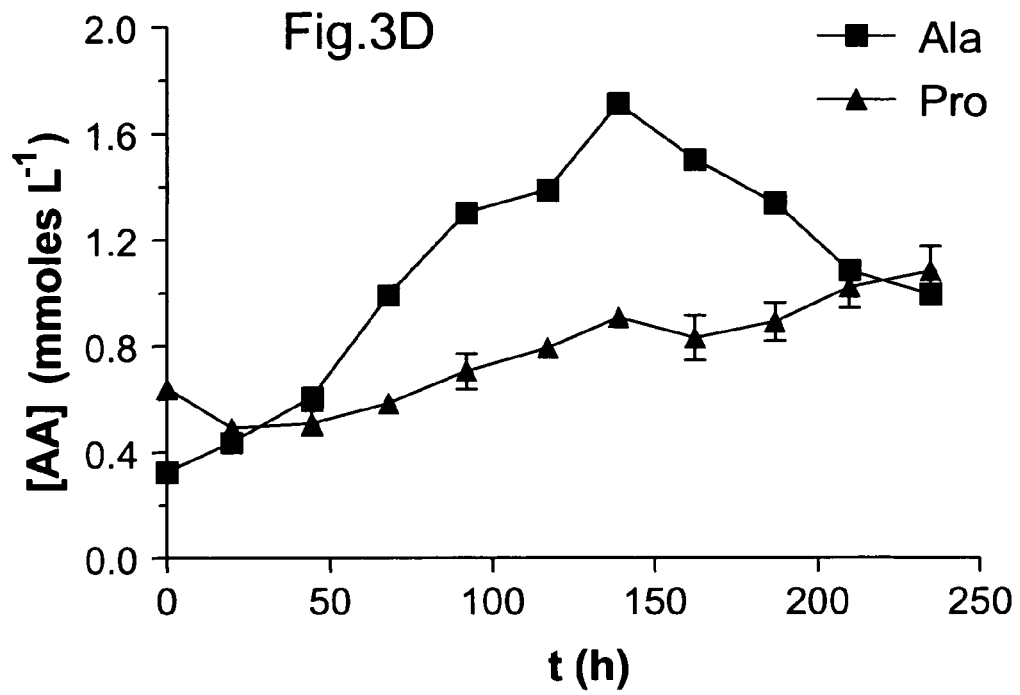
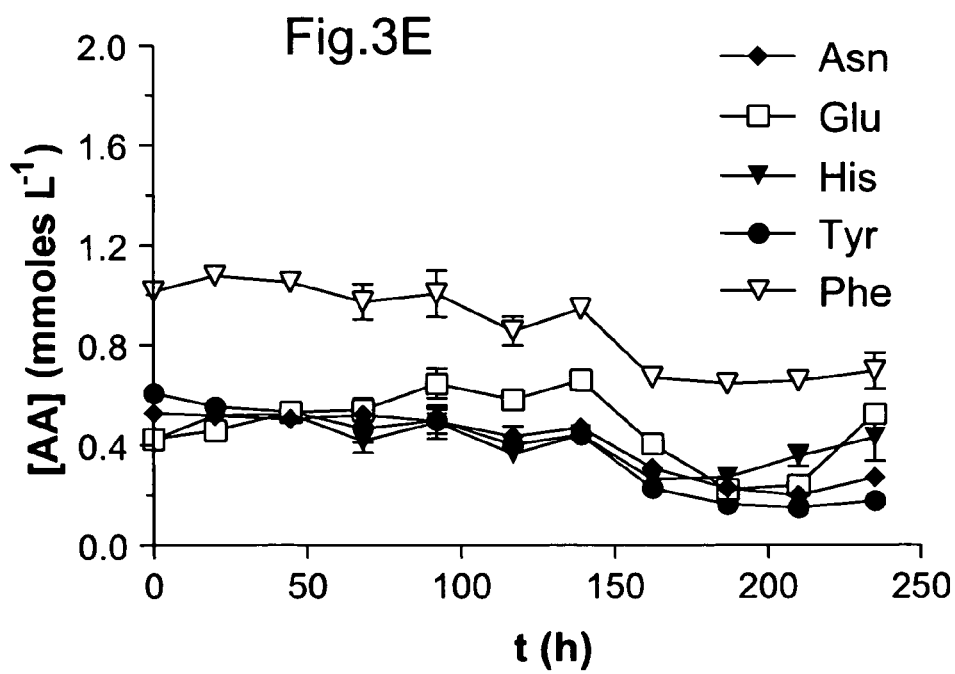

PROCESSES FOR CULTURING E1-IMMORTALIZED CELLS TO INCREASE PRODUCT YIELDS

CROSS-REFERENCE TO RELATED APPLICATIONS

This application is a continuation of International Patent Application PCT/EP2004/050724, filed May 6, 2004, designating the United States of America, published, in English, as International Patent Publication WO 2004/099396 A1 on Nov. 18, 2004, which itself claims priority from International Patent Application Nos. PCT/EP03/50155 filed May 9, 2003, PCT/EP03/50390 filed Sep. 1, 2003, PCT/EP03/50940 filed Dec. 4, 2003, and PCT/EP04/050061 filed Jan. 30, 2004, the contents of the entirety of each of which are incorporated herein by this reference.

FIELD OF THE INVENTION

The invention relates generally to biotechnology in area of cell culture. In particular, the invention relates to the field of culturing cells derived from cells that have been immortalized with E1 sequences from adenovirus. More in particular, the invention relates to culturing such cells to obtain high levels of products from such cells.

BACKGROUND OF THE INVENTION

A human PER.C6® cell line, exemplified by cells deposited at the ECACC under No. 96022940, derived from retina cells by immortalization with the adenovirus (Ad5) E1a and E1b genes is disclosed in U.S. Pat. No. 5,994,128. Besides the ability to function as packaging cells for E1-deleted adenoviral vectors (U.S. Pat. No. 5,994,128; WO 01/005945), and for producing other viruses (WO 01/38362), E1-immortalized cells, such as PER.C6 cells, can be used to produce recombinant proteins, such as antibodies (WO 00/63403).

Xie et al. (2002) have disclosed a process for serum-free suspension cultivation of E1-immortalized cells. However, the product yields obtained using the culturing processes disclosed in the art for E1-immortalized cells, can be improved.

SUMMARY OF THE INVENTION

In particular embodiments, the present invention provides processes to increase the product yield from E1-immortalized cells.

In certain embodiments, the invention provides feed strategies for fed-batch or fed-perfusion cultures of cells immortalized by adenovirus E1 sequences. In one embodiment thereof, the invention provides a method for the culturing of such cells, the cells capable of growing in suspension, comprising the steps of: determining at least once during the culturing of the cells the concentration of at least one medium component selected from the group consisting of glucose, glutamine phosphate, leucine, serine, isoleucine, arginine, methionine, cystine, valine, lysine, threonine and glycine, adding components to the medium during the culturing of the cells at or prior to the depletion of at least one of the components of which the concentration was determined in the previous step, wherein the components added at least comprise glucose, glutamine, phosphate, leucine, serine, isoleucine, arginine, methionine, and cystine. Other components that beneficially may be added according to the invention, amounts and time of addition of the components are provided herein below, as well as in the claims.

In another embodiment, the invention provides a culture of cells derived from cells immortalized by adenovirus E1 sequences, characterized in that the culture comprises at least $10 \times 10^6$ cells/ml. Preferably, the culture comprises at least $12 \times 10^6$ cells/ml, more preferably, at least $15 \times 10^6$ cells/ml. In certain preferred embodiments, the culture according to the invention comprises more than $20 \times 10^6$, $25 \times 10^6$, $30 \times 10^6$ or $40 \times 10^6$ cells/ml. Methods to obtain such cultures are also provided herein.

In yet another aspect, a method to increase cell densities and product yields from a culture of cells immortalized by adenovirus E1 sequences is provided. In one embodiment hereof, a process for culturing such cells is provided, characterized in that the process comprises a step of subculturing the cells at a seeding concentration of between $0.8 \times 10^6$ and $2.0 \times 10^6$ viable cells/ml, preferably, between $0.9 \times 10^6$ and $1.5 \times 10^6$ viable cells/ml.

Preferably, the cells used in the methods of the invention are derived from retina cells, more preferably, from human embryonic retina (HER) cells, such as the cells deposited under ECACC No. 96022940. In certain embodiments, the cells are PER.C6 cells.

In certain embodiments, the cells can produce recombinant proteins, preferably, antibodies, at high yields. In other embodiments, the cells comprise recombinant adenoviral vectors having a deletion in the E1-region, or other viruses, which can be produced on the cells in high yields using the process according to the invention. In preferred embodiments, the cells are cultured at least part of the time in a serum-free medium.

DETAILED DESCRIPTION OF THE INVENTION

Figure 1:
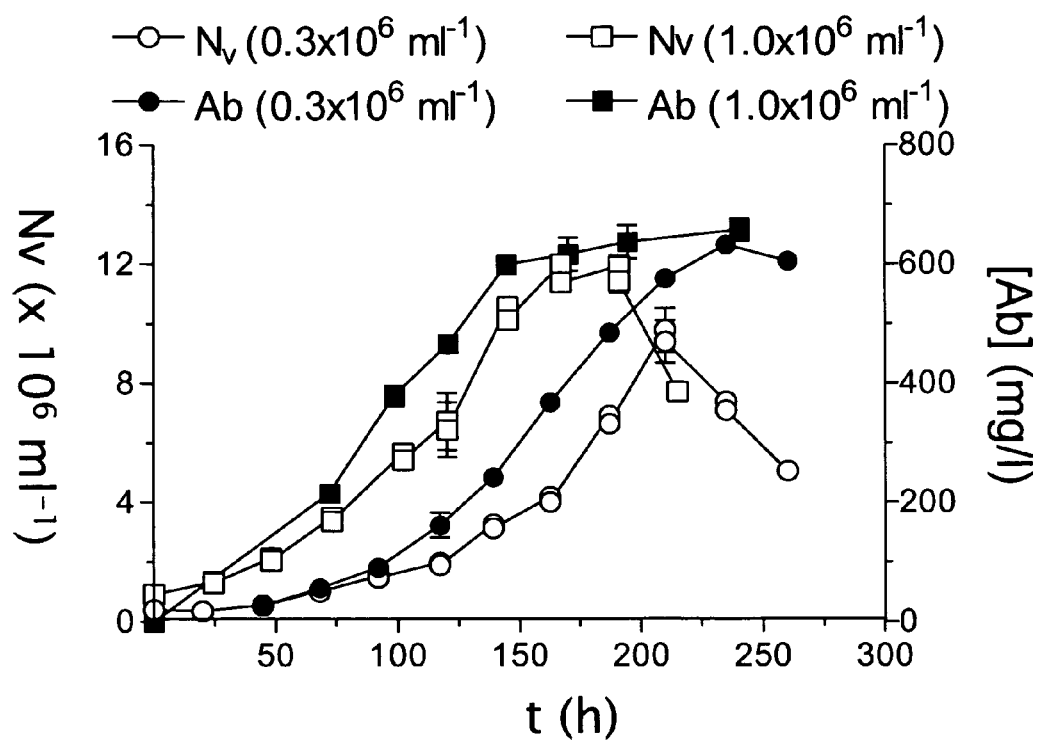
FIG. 1. Graph showing growth and antibody production of a PER.C6 clone (clone 1) grown in shake flask at two different starting cell concentrations (0.3 and $1.0 \times 10^6$/ml). Left vertical axis: viable cell number ($N_v$). Right vertical axis: antibody (Ab) concentration. Horizontal axis: time (hours).

The productivity of any cell line is mainly defined by three basic parameters, the specific productivity of the cell line, the peak viable cell concentration that is attainable and the length of the production process that is possible. Increases in either of these variables will lead to increases in the final product concentration and is dependent to a large extent on the cell line. In a straight batch culture, cell lines such as CHO and SP2/0 can achieve cell densities up to $4 \times 10^6$/ml. In fed-batch or perfusion processes the viable cell concentration is increased, and typically hybridoma cells such as SP2/0 can be cultured up to $10 \times 10^6$ cells/ml, while CHO can be cultured up to $6\text{-}10 \times 10^6$ cells/ml. The invention describes methods to increase the viable cell density of cultures of cells immortalized by adenovirus E1 sequences, preferably, derived from embryonic retina cells, to attain cell densities beyond those reported in the prior art. Furthermore, the methods according to the invention can be used to obtain higher product yields from cultures of cells according to the invention.

Disclosed herein are improvements in how E1-immortalized cells, such as PER.C6® cells (available from Crucell, Leiden, NL), can advantageously be used for the production of high yields of monoclonal antibodies. It is disclosed that these cells be cultured to very high viable cell concentrations in a straight batch process (e.g., up to $14 \times 10^6$ viable cells/ml).

Furthermore, E1-immortalized cells, such as PER.C6® cells, are well suited to a fed-batch process as a culture of these cells unexpectedly consumes lactate and ammonia and maintains viability for long periods of time under nutrient limiting conditions. Methods to increase product yields from the cells by a feed strategy in cultures are provided herein.

With the term "feed strategy" as used herein is meant the addition of certain identified components including, but not limited to, nutrients, such as sugars, amino acids, and the like, to the culture medium. The identified components are, preferably, added in certain amounts and at certain times, when they are required to improve product yields from the cells, such as provided herein.

E1-immortalized cells, such as PER.C6® cells, are also well suited to a perfusion process as they can be maintained at very high viable cell concentrations (up to $50 \times 10^6$ cells/ml with a viability of at least 85%) for long periods of time and with good final product concentrations.

Culture Media

The processes of the invention generally increase the product yields from the cells compared to yields obtained with processes described in the art for the cells according to the invention. Preferably, serum-free culture media are used at least part of the time in the processes according to the invention. Preferably, the medium contains only recombinantly produced proteins, which are not of animal origin. Such culture media are commercially available from various sources. In one embodiment of the invention, VPRO culture medium (JRH Biosciences) is used for the fed-batch or (fed-)perfusion process.

Products

The methods of the invention are, preferably, used to produce products in cells of the invention. The processes of the present invention can be used for the improved production of antibodies, as well as other proteins (WO 00/63403, the contents of which are incorporated by herein by this reference). For the production of proteins, the cells of the invention suitably comprise nucleic acid encoding the proteins, in operable association with elements capable of driving expression of the proteins. Furthermore, the processes can be used for improvement of the production of recombinant adenoviral vectors having a deletion in the E1-region, in which case the cells are used as complementing cells, which in itself is known to the skilled person according to established methodology (e.g., U.S. Pat. No. 5,994,128; WO 01/005945, the contents of both of which are incorporated herein by this reference). Moreover, the processes according to the invention can be used to improve a process for propagation of other (non-adenovirus) viruses in the cells (WO 01/38362, the contents of which are incorporated herein by this reference). Hense, products according to the invention can be recombinant proteins, such as antibodies, erythropoietin, and the like, as well as recombinant adenoviral vectors with a deletion in the E1 region, or other viruses.

Cells

The cells according to the invention are cells that have been immortalized with E1 sequences from an adenovirus, which cells are also referred to herein as E1-immortalized cells. Such cells express at least a functional part of the E1A region of an adenovirus, and, preferably, also at least a functional part of the E1B region. E1A protein has transforming activity, while E1B protein has anti-apoptotic activities. The cells according to the invention may be derived from any cell, including lung cells, kidney cells, amniocytes, but, preferably, are derived from retina cells. They may be derived from embryonic retina cells. Preferably, the cells according to the invention are human cells. A method for immortalization of embryonic retina cells has been described in the art (U.S. Pat. No. 5,994,128). Accordingly, a retina cell that has been immortalized with E1 sequences from adenovirus can be obtained by that method. In certain preferred embodiments, the cells of the invention are derived from E1-immortalized HER cells, such as PER.C6 cells. PER.C6 cells for the purpose of the present application shall mean cells from an upstream or downstream passage or a descendent of an upstream or downstream passage of cells as deposited under ECACC No. 96022940. In addition, also the E2A region with a ts125 mutation may be present (see e.g., U.S. Pat. No. 6,395,519, the contents of which are incorporated herein by this reference) in the cell. A cell derived from a PER.C6 cell can be a PER.C6 cell infected with recombinant adenovirus or other virus, and can also be a PER.C6 cell into which recombinant nucleic acid has been introduced, for instance, comprising an expression cassette wherein nucleic acid encoding a protein of interest is operably linked to sequences capable of driving expression thereof, such as a promoter and polyA signal, wherein, preferably, the cells are from a stable clone that can be selected according to standard procedures known to the person skilled in the art.

A culture of such a clone is capable of producing a protein encoded by the recombinant nucleic acid.

Components for Feed Strategies

In one aspect, the invention provides processes for culturing cells according to the invention, wherein by feed strategies according to the invention certain amino acids are added during the culturing process to replenish amino acids of which the concentration has become or will become limiting for an optimal process and product yields. By amino acid is intended all naturally occurring alpha amino acids in both their D and L stereoisomeric forms, and their derivatives. A derivative is defined as an amino acid that has another molecule or atom attached to it. Derivatives would include, for example, acetylation of an amino group, amination of a carboxyl group, or oxidation of the sulfur residues of two cysteines to form cystine. Further, amino acid derivatives may include esters, salts, such as chlorides, sulphates, and the like, as well as hydrates. It will be understood by the person skilled in the art, that where a specific amino acid is mentioned herein, a derivative may also be used and is meant to be included within the scope of the invention. Other components such as sugars, growth factors, vitamins, etc., may also be added to improve the processes according to the invention.

Feed Strategies

In one aspect, the invention provides a method for producing a product in cells immortalized by adenovirus E1 sequences, in a culture medium, wherein the product is chosen from the group consisting of a recombinant protein, a virus, and a recombinant adenovirus with a deletion in the E1 region, characterized in that the method comprises a step wherein at least leucine, serine, isoleucine, arginine, methionine and cystine are added to the culture medium. In one aspect the invention provides a method for the culturing of cells immortalized by adenovirus E1 sequences, the cells capable of growing in suspension, comprising the steps of: determining at least once during the culturing of the cells the concentration of at least one medium component selected from the group consisting of glucose, glutamine, phosphate, leucine, serine, isoleucine, arginine, methionine, cystine, valine, lysine, threonine and glycine, adding components to the medium during the culturing of the cells at or prior to the depletion of at least one of the components of which the concentration was determined in the previous step, wherein the components added at least comprise glucose, glutamine, phosphate, leucine, serine, isoleucine, arginine, methionine and cystine. "Depletion" as used herein is defined as the time a component has a concentration of 30% or less of the starting concentration in the culture medium. In these aspects, the determination of the concentration of at least one medium component selected from the group consisting of glucose, glutamine, phosphate, leucine, serine, isoleucine, arginine, methionine or cystine is preferred over the determination of only components selected from the group consisting of valine, lysine, threonine and glycine. In certain embodiments, the concentration of at least two medium components according to the invention is determined in the first step. In certain embodiments, the components that are added further comprise one or more of valine, lysine, threonine, glycine, asparagine, tyrosine, histidine, phenylalanine, tryptophan, calcium, LongR3 IGF-1, Long EGF and insulin. In specific embodiments, the components are added in an end concentration in mmoles/l of freshly added component per $10\times10^6$ cells/ml of 6.0 for glucose, 2.60 in the first feed and 1.75 in subsequent feeds for glutamine, 0.70 for phosphate, 0.66 for leucine, 1.10 in the first feed and 0.55 in subsequent feeds for serine, 0.50 for isoleucine, 0.46 for arginine, 0.23 for methionine, and 0.25 for cystine. In further embodiments, the following components are further added to an end concentration in mmoles/l of freshly added component per $10\times10^6$ cells/ml of 0.45 for valine, 0.44 for lysine, and 0.30 for threonine. In further embodiments, the following components are further added to an end concentration in mmoles/l of freshly added component per $10\times10^6$ cells/ml of 0.10 for asparagine, 0.13 for tyrosine, 0.10 for histidine, 0.02 for phenylalanine, and 0.06 for tryptophan. Furthermore, calcium may be added in an end concentration in mmoles/l of freshly added component per $10\times10^6$ cells/ml of 0.02. Growth factors such as IGF, EGF, and insulin or their derivatives may also suitably be present in the growth medium. The amounts for the addition of components above may have an error margin per component of 33% or less, preferably, 20% or less, more preferably, 10% or less, even more preferably, 5% or less. The amounts are presented per $10\times10^6$ cells/ml, and are linearly dependent on the number of cells/ml. In preferred embodiments, the components are added at between 48 hours and the moment of depletion of at least one of the medium components the concentration of which was determined in the previous step. In certain embodiments, the addition is at a time between 24 hours and just prior to depletion. In certain aspects, the invention provides a method according to the invention, wherein the cells express a recombinant immunoglobulin that is secreted into the culture medium to a level of at least 500 mg per liter, preferably, at least 700 mg/l, more preferably, at least 850 mg/l, even more preferably, at least 1000 mg/l, still more preferably, at least 1250 mg/l, still more preferably, at least 1500 mg/l, still more preferably, at least 1750 mg/l and still more preferably, at least 2000 mg/l. In general, the addition of medium components according to the invention in, for instance, a fed-batch process, results in an increase in the yield of produced product of at least 1.5×, preferably, at least 2×, more preferably, at least 2.5× and still more preferably, about 3× or even higher, compared to the process wherein no components are added, i.e., the batch process.

In addition to use in a fed-batch process, the feed strategies of the invention can also be beneficially used in an optimized batch process, as set out in Example 5.

Perfusion

Figure 3A:
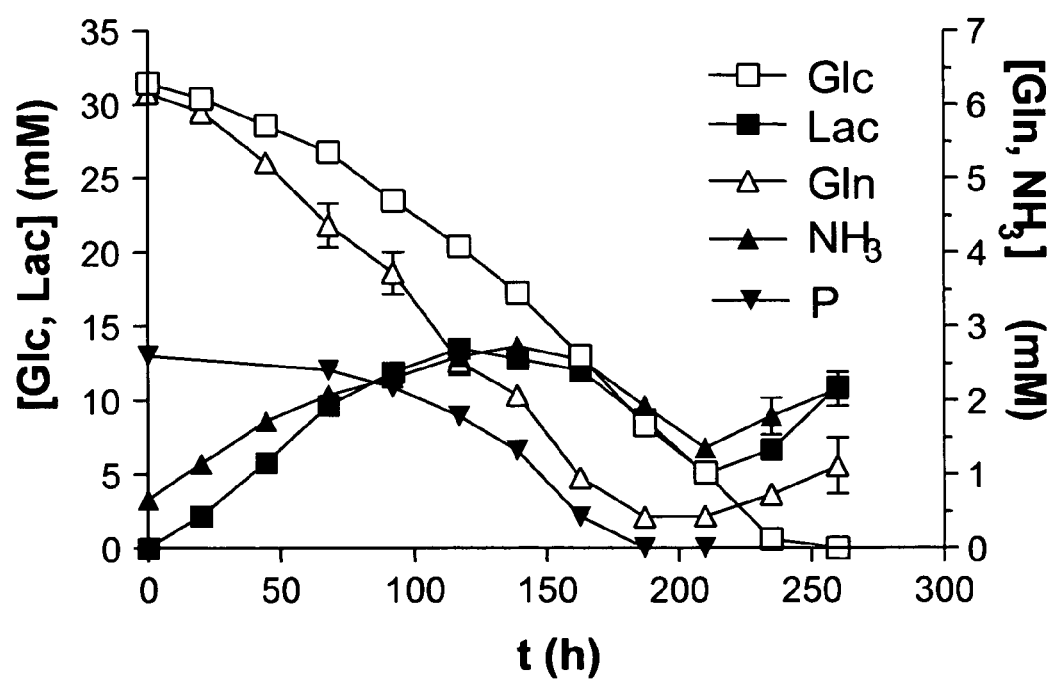
FIG. 3. Profiles for a batch culture of PER.C6® clone 1. A: Metabolites. Glc, glucose; Lac, lactate; Gln, glutamine; $NH_3$, ammonia; P, phosphate. B-E: Amino acids (AA).
Figure 5:
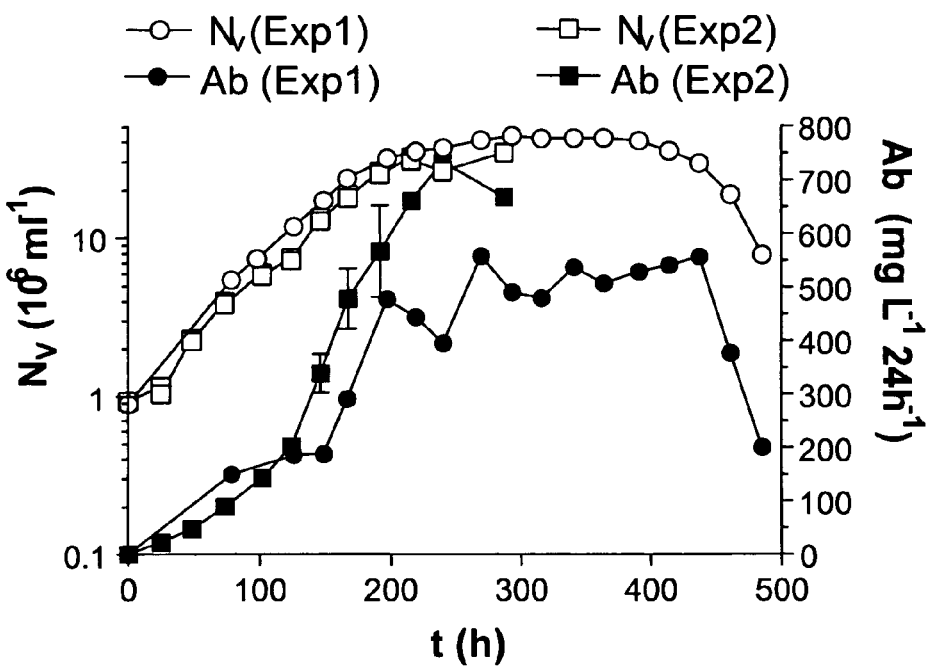
FIG. 5. Graph showing viable cell numbers ($N_v$) and antibody (Ab) yields of PER.C6 clones where culture medium was completely exchanged once per day (two independent experiments each). A: clone 1. B: clone 2.
Figure 5:
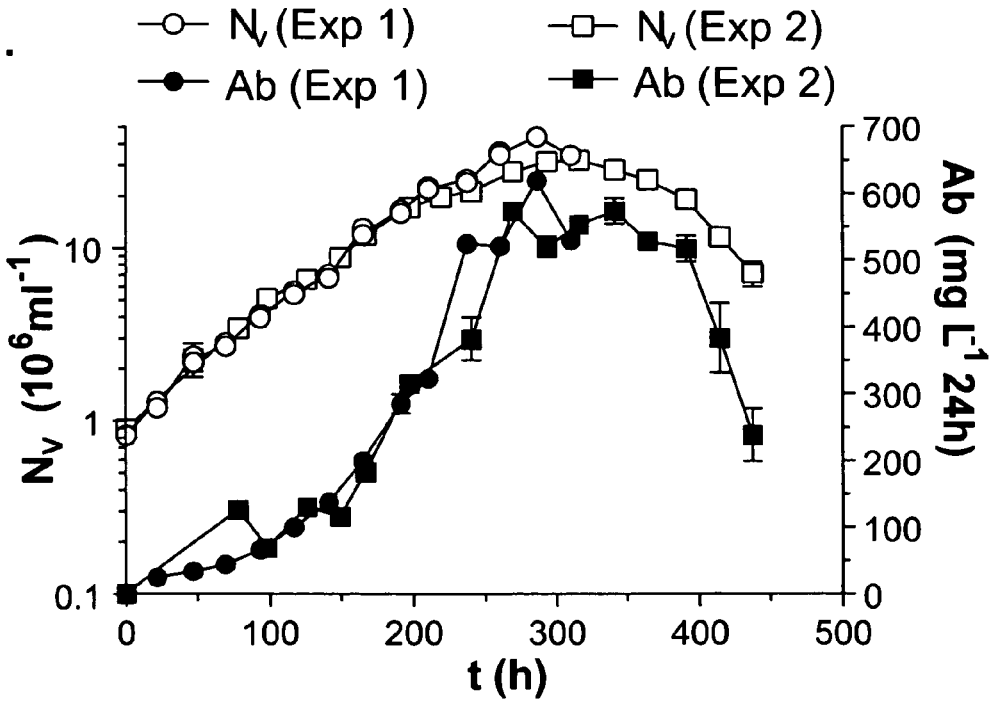

Alternatively, in another aspect of the invention, the entire culture medium may be exchanged. It is shown that unexpected high viable cell densities can be attained when this is applied to cells derived from retina cells immortalized by adenovirus E1 sequences. Exchanging culture medium may be performed by any means known to the person skilled in the art, including, but not limited to, collection of the cells by centrifugation, filtration, and the like, followed by re-suspension of the cells into fresh culture medium. Alternatively, a perfusion system may be used, wherein culture medium is either continuously or intermittently exchanged using a cell separation device such as a Centritech centrifuge or passage through a hollow fiber cartridge, and the like. It is, therefore, another aspect of the invention to provide a process for culturing cells derived from embryonic retina cells immortalized by adenovirus E1 sequences, characterized in that culture medium is exchanged at a rate of 0.2-3, preferably, 0.5-3, culture volumes per day (24 hours). Cultures obtained using this method, preferably, have viable cell densities higher than $20\times10^6$ cells/ml, more preferably, higher than $30\times10^6$ cells/ml. In certain aspects, such cultures have cell densities higher than $40\times10^6$ cells/ml. In certain aspects such cultures are used to produce recombinant antibodies with a yield of at least 150 mg/l/day, preferably, at least 200 mg/l/day, more preferably, at least 300, 400, or 500 mg/l/day. Of course, also other products according to the invention can be produced by such methods. It is shown here that one complete volume exchange of culture medium each day supports at least $30 \times 10^6$ viable cells/ml with antibody yields of more than 500 mg/L/day (up to 750 mg/l/day) (FIG. 5). One complete medium exchange per day corresponds to a continuous perfusion rate of three volumes per day, meaning that a continuous perfusion system could yield approximately at least 150-200 mg/L/day. One method to reduce this perfusion rate and, thus, increase antibody yields (by reducing the volume in which the antibody is secreted) is to supplement the fresh culture medium with the essential components (known as fed-perfusion). These components for antibody-producing E1-immortalized cell, such as PER.C6 cell, clones are identified herein (see Example 2) and therefore it is another aspect of the present invention to provide such a fed-perfusion system, wherein the feed strategies, according to the present invention, are employed. A common drawback of fed-perfusion processes is the build-up of toxic metabolic by-products (such as lactate and ammonia), which can result in low cell viabilities and product yields. There is often a requirement at high cell concentrations for a high perfusion rate to remove these by-products. One advantage demonstrated for E1-immortalized cell, such as PER.C6 cell, clones according to the invention is that they are capable of utilizing lactate and ammonia such that concentrations do not become problematical (see, FIG. 3A). It is, therefore, possible to obtain an antibody yield of at least 500 mg/l/day by changing the culture medium once or twice a day. Alternatively, this can be achieved by using a continuous perfusion rate of, for instance, one volume per day in combination with supplementation of the medium with a feed concentrate (fed-perfusion). This can advantageously be combined with a cell bleed (removing a certain percentage of the cells population).

Cultures with high cell densities are advantageous for obtaining high product yields. It is, therefore, another aspect of the invention to provide a culture of cells derived from cells immortalized by adenovirus E1 sequences, the culture comprising at least $10 \times 10^6$ cells/ml. The viability in the culture is at least 80%. Preferably, the viability is at least 90%, more preferably, at least 95%. The cultures according to the invention are, preferably, suspension cultures, meaning that the cells in the cultures are in suspension in the culture medium, such as in shake flasks, roller bottles, bioreactors, including stirred tanks, air lift reactors, and the like. The strategies disclosed herein may, however, also be used for cultures of cells in hollow fiber reactors, such as described by Tanase et al. (1997), and for adherent cultures, such as cells on microcarriers. In one embodiment, the culture comprises at least $12 \times 10^6$ cells/ml. It is disclosed herein that up to $14 \times 10^6$ cells/ml can be obtained by a straight batch culture.

It is further demonstrated that, using medium perfusion, even higher cell densities can be achieved, for example, up to $50 \times 10^6$ cells/ml. The prior art does not provide any indication that such unexpected high cell densities are obtainable. In other preferred embodiments, therefore, the invention provides a culture of cells derived from E1-immortalized cells, preferably, derived from retina cells, the culture comprising at least $15 \times 10^6$ cells/ml, preferably, at least $20 \times 10^6$ cells/ml, more preferably, at least $25 \times 10^6$ cells/ml. In specific embodiments, the culture comprises at least $30 \times 10^6$ cells/ml, or even at least $40 \times 10^6$ cells/ml.

Cultures with at least $15 \times 10^6$ cells/ml, according to the invention, appear obtainable by a perfusion process, meaning that culture medium is exchanged during the culturing process. The cultures, according to the invention, have a viability of at least 80%, preferably, at least 85%, more preferably, at least 90%, still more preferably, at least 95%. The cultures are suspension cultures. The cultures further comprise growth medium. The growth medium, preferably, is serum-free. The cells of the culture may comprise recombinant nucleic acid molecules encoding immunoglobulins, or parts or derivatives thereof, in expressible format. Such cells are capable of producing immunoglobulins in high yields. In particular, it is shown herein that a culture of cells, according to the invention, wherein the medium is exchanged every day, and wherein more than $30 \times 10^6$ cells/ml are present, can provide recombinant antibody yields of at least 500 mg/l/day. The cells in the culture, preferably, produce at least 10 pg protein/cell/day.

The processes of the invention, especially those for recombinant protein production, can also be combined with other measures described in the art that in some cases improve product yields. Therefore, in certain embodiments of the invention, the culture medium is subjected to a temperature shift before or during the production phase, e.g., by running the process at a lower temperature, for instance, between 30° C. and 35° C., in the production phase (see e.g., U.S. Pat. No. 6,506,598, the contents of which are incorporated herein by this reference, and literature cited therein, which describes effects of lowering the cell culture temperature on several parameters for recombinant protein production), or by the addition of cold culture medium to the culture (wherein cold is meant to be lower than the temperature the cells are cultured in, preferably, the cold culture medium having a temperature between 2° C. and 8° C.) when the cells are subcultured or later during the culture process. In other embodiments, specific growth factors may be added to improve the processes according to the invention with regard to product yields. In yet other embodiments, for the production of proteins, the processes, according to the invention, may be improved by the addition of alkanoic acids or salts thereof, such as sodium butyrate, either during the whole culture phase or only during the production phase (see, e.g., U.S. Pat. No. 6,413,746, and references therein, which describes effects of addition of butyrate on production of proteins in cell culture). In yet other embodiments for the production of proteins, the culture medium is subjected to a temperature or pH shift (Weidemann et al., 1994, Sauer et al., 2000).

It will be clear to the person skilled in the art that several aspects and/or embodiments, according to the invention, can be combined to provide a process for culturing cells which leads to particularly good product yields. As a non-limiting example, it is, for instance, possible to seed a culture of E1-immortalized cells at about $0.8 \times 10^6$ to $2.0 \times 10^6$ cells/ml, and use a feed strategy and/or exchange the growth medium during the culturing process to improve the final product yields.

The invention will now be illustrated with some examples, not intended to limit the scope of the invention.

Experimental

Methods and vectors for genetically engineering cells and/or cell lines to express a protein of interest are well known to those of skill in the art; for example, various techniques are illustrated in Current Protocols in Molecular Biology, Ausubel et al., eds. (Wiley & Sons, New York, 1988, and quarterly updates) and Sambrook et al., Molecular Cloning: A Laboratory Manual (Cold Spring Laboratory Press, 1989). General and standard cell culture techniques are known to the person skilled in the art, and are, for instance, described in R. I. Freshney, Culture of animal cells: A manual of basic technique, fourth edition (Wiley-Liss Inc., 2000, ISBN 0-471-34889-9). Such standard techniques were followed unless otherwise noted.

Cell Culture Protocols

PER.C6® cells were cultured in the examples. Cells were adapted from adherent cultures in DMEM containing 10% FBS (Invitrogen) to serum-free medium by direct transfer. Briefly, sub-confluent, logarithmic cells were trypsinized, washed once with serum-free medium and inoculated directly into 250 ml Erlenmeyer flasks with a 0.21 µ filter (Corning), containing 25 ml of ExCell-525 serum-free medium (JRH Biosciences) at a starting cell concentration of 0.3-0.5×10$^6$ ml$^{-1}$, unless otherwise noted. Cultures were maintained in logarithmic growth in Erlenmeyer flasks by passage every two to three days. Flasks were shaken on a magnetic shaker platform (Infors) at 100 rpm in a humidified incubator at 37° C. and 5% $CO_2$. Cultures were passaged by centrifugation at 1000 rpm for 5 minutes. The supernatant was removed and the pellet re-suspended in the remaining medium. Fresh, cold medium (4° C.) was added and new flasks inoculated at the appropriate cell concentration. After transfer to serum-free medium, cultures were passaged for two to four weeks to allow for complete adaptation, after which a serum-free cell bank was created. All experiments were started using cells from this cell bank.

Bioreactors

Bioreactor cultures were performed in 3L reactors with a 2L working volume (Applikon). Temperature was maintained at 37° C. by a heating blanket. Dissolved oxygen concentration ($dO_2$) was controlled at 50% of air saturation by adjusting inlet gas composition through the headspace and intermittent sparging through a microporous sparger. Starting culture pH was controlled at 7.3 by $CO_2$ addition through the microporous sparger. The lower culture pH limit was set at 6.7 so that the culture pH was allowed to drift downwards (the lower limit was not reached). Cultures were agitated by two marine impellers at 75 rpm. Process data was acquired by the BioExpert software (Applikon).

Analytical Protocols

Cell counts and viability measurements were performed using a CASY automatic cell counter (Scharfe Systems). Glucose, lactate, ammonia and phosphate concentrations were determined using an EKTACHEM II® analyzer (Kodak) with cell-free culture supernatants. Amino acid concentrations were determined using a modified AccuTag HPLC method (Waters) as described by van Wandelen and Cohen (1997). Aliquots (200 µl) of centrifuged culture supernatant were stored at −20° C. in 1 ml cryovials (Nalgene) until required. Samples from each experiment were analyzed at the same time to avoid experimental variation. Osmolality was measured by a freezing point depression osmometer (Osmomat 030-d, Gonotec). Antibody concentration was determined by a sandwich-type ELISA. Briefly, plates were coated with 2 µg ml$^{-1}$ mouse anti-human IgG against the kappa light chain (Pharmingen) and incubated overnight at 4° C. An HRP-conjugated mouse anti-human IgG against the heavy chain (Pharmingen; 1:500) was used as detection antibody for one hour at 37° C. with OPD (Sigma) as substrate. Washing between incubation steps was performed with 0.05% Tween 20 in PBS. Samples were diluted in washing buffer supplemented with 0.1% BSA.

Quantification was relative to an IgG1 reference standard using a calibration range of 10 to 400 ng ml$^{-1}$. Antibody samples purified by Protein A were subject to quality analysis by isoelectric focusing (IEF) and denaturing polyacrylamide gel electrophoresis (SDS-PAGE). For glycan analysis, N-linked glycans were removed by PNGase F treatment of the IgG samples in 20 mM sodium phosphate (pH 7.2) and analyzed with MALDI-MS in the reflector mode on an Applied Biosystems Voyager DE Pro mass spectrometer. The matrix was 2,5-dihydroxybenzoic acid (10 mg ml$^{-1}$) in 50/50/0.1 acetonitrile/water/trifluoroacetic acid. Spectra were obtained in the positive ion mode and glycans were detected as sodium adducts, [M+Na]+.

Calculation of Cell Specific Metabolic Rates

Cell specific rates of metabolite utilization and production in batch and fed-batch culture were calculated using the log mean of the cell concentration as shown in the following equation:

$$q_s = (C_2 - C_1)/(t_2 - t_1) \times [(X_2 - X_1)/\ln(X_2 - X_1)].$$

In this equation, C is the metabolite concentration (µmoles/l), t is time (days) and X is the viable cell concentration. A rate constant accounting for the spontaneous decomposition of glutamine was not included as decomposition was not significant at the time points at which the rates were calculated (data not shown). The yield coefficients of lactate produced per glucose ($Y_{lac/glc}$), ammonia produced per glutamine ($Y_{amm/gln}$) and alanine produced per glutamine ($Y_{ala/gln}$) were calculated from the equations below and are expressed in mole/mole:

$$Y_{lac/glc} = q_{lac}/q_{glc}$$

$$Y_{amm/gln} = q_{amm}/q_{gln}$$

$$Y_{ala/gln} = q_{ala}/q_{gln}$$

EXAMPLES

Example 1

Increasing Maximum Final Cell Yields in Batch Culture of PER.C6 Cells

The simplest production process is a batch culture. However, this is restricted in the viable cell concentration and therefore the product yields attainable, due largely to nutrient limitation. A method is presented to increase the maximum final cell concentration of a batch culture of PER.C6® or PER.C6-derived sub-clones by calculating the cell specific rate of utilization of key nutrients at different cell concentrations and starting the batch culture at a cell concentration where there is optimal utilization of nutrients with respect to cell growth.

The DNA encoding the antigen-binding region of an antibody recognizing epithelial cell adhesion molecule (EpCAM) was first isolated from a scFv phage display library (Huls et al., 1999). DNA encoding the antigen-binding region of an antibody recognizing CD46 was isolated as disclosed in WO 02/018948, the contents of which are incorporated by this reference. A leader sequence and constant regions of IgG1 type were added essentially as described in Boel et al., 2000. The DNA encoding the light and heavy chains were then cloned into expression vector pcDNA3002(Neo). The expression vector pcDNA3002 (Neo), which has been described in international patent application PCT/NL02/00841, was deposited on Dec. 13, 2001, at the European Collection of Cell Cultures (ECACC) under Number 01121318. The resulting expression vectors, encoding an IgG1 that recognizes EpCAM or CD46, respectively, regulated by a CMV promoter, was introduced in PER.C6 cells according to standard methods.

A recombinant antibody-expressing clone, derived from a parental population of the PER.C6® cell line, was used in these experiments. The clone expressing anti-EpCAM is further referred to herein as clone 1, the clone expressing anti-CD46 is further referred to herein as clone 2.

Cells were maintained in EXCELL™ 525 medium (JRH Biosciences) (maintenance of the cells in GTM-3 medium (Sigma) did also work) and batch productions were carried out in EXCELL™ VPRO medium (JRH Biosciences, Cat. No. 14560). Cells were transferred directly from EXCELL™ 525 to EXCELL™ VPRO for the batch productions.

FIG. 1 shows that the maximum final viable cell concentration of cultures started at $1 \times 10^6$ cells ml$^{-1}$ reached almost $14 \times 10^6$ cells ml$^{-1}$ after six days (approximately three-fold higher than batch cultures of CHO and Sp2/0), compared to cultures started at $0.3 \times 10^6$ ml$^1$, which reached $10 \times 10^6$ cells ml$^{-1}$ after nine days. There is very little difference in the final antibody titers of both cultures. However, in the culture started at $1 \times 10^6$ ml$^{-1}$, approximately 600 mg L$^{-1}$ was reached after six days, compared to nine days for the cultures started at $0.3 \times 10^6$ ml$^{-1}$.

The higher cell concentrations observed in cultures started at $1 \times 10^6$ cells ml$^{-1}$ compared to $0.3 \times 10^6$ ml$^{-1}$ is due to the lower cell specific rate of nutrient utilization at the higher cell concentration. The respiration rate of hybridoma cells has been shown to decrease with increasing cell density (Wohlpart et al., 1990). Similarly, the cell specific rate of utilization of a nutrient has also been shown to decrease with increasing cell concentration (Portner et al., 1994, Yallop and Svendsen 2001). We have now used this information in a novel and inventive way to form a concept for increasing attainable cell densities in a culture.

Figure 2:
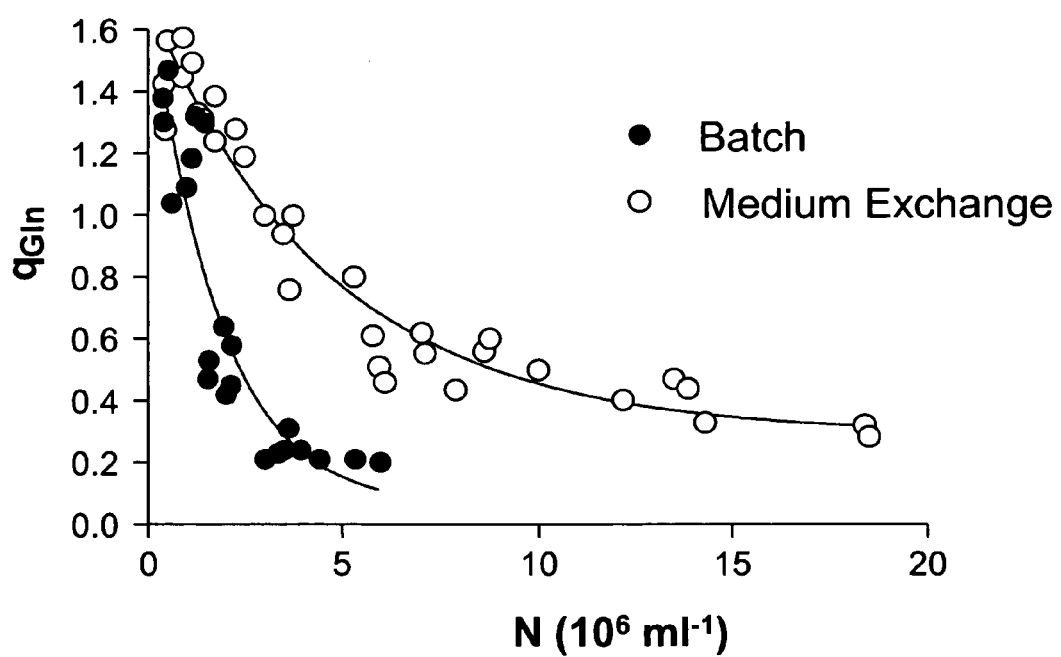
FIG. 2. Graph showing the decrease in the cell specific utilization of glutamine with increasing viable cell numbers for an antibody-producing PER.C6® clone (clone 1). N: cell number.

By calculating the cell specific rate of utilization of a key nutrient each day in a batch culture and plotting these values against cell concentration, a graph can be obtained as shown in FIG. 2 for glutamine. FIG. 2 shows the relationship between the cell specific rate of glutamine utilization ($q_{Gln}$) and cell concentration. From this graph, an optimum starting cell concentration can be selected based on optimal use of the available nutrients. For example, a culture starting at $0.3 \times 10^6$ cells ml$^{-1}$ will reach approximately $0.5 \times 10^6$ ml$^{-1}$ in 24 hours (average population doubling time (pdt) of this clone is 32 hours). The $q_{Gln}$ value at $0.5 \times 10^6$ cells ml$^{-1}$ is approximately 2.5 µmoles $10^6$ cells$^{-1}$ 24 hours$^{-1}$. The total glutamine consumed in this 24 hours will, therefore, be approximately 1.25 µmoles ml$^{-1}$ ($0.5 \times 2.5$). However, a culture starting at $1 \times 10^6$ cells ml$^{-1}$ will reach approximately $1.5 \times 10^6$ ml$^{-1}$ in 24 hours. The $q_{Gln}$ value at this cell concentration is approximately 0.75 µmoles $10^6$ cells$^{-1}$ 24 hours$^{-1}$. The total glutamine consumed will therefore be approximately 1.125 µmoles ml$^{-1}$. The two cultures will therefore use approximately the same amount of glutamine in the first 24 hours.

It is, therefore, another object of the invention to provide a method of culturing cells, comprising starting a culture at a cell concentration where the specific nutrient utilization level is close to a minimum plateau level. This equates with around 0.8 to $2.0 \times 10^6$ cells/ml, preferably, $0.9$-$1.5 \times 10^6$ cells/ml, for E1-immortalized retina cells, particularly, PER.C6-derived cells. It is, therefore, an embodiment of the invention to subculture the cells at a seeding concentration of $0.8$-$2.0 \times 10^6$ cells/ml, preferably, $0.9$-$1.5 \times 10^6$ cells/ml, more preferably, $0.95$-$1.25 \times 10^6$ cells/ml.

The advantage of this aspect of the invention is that the number of viable cells that can be obtained is higher at this higher seeding density, and higher numbers of cells are reached faster during the process. This aspect of the invention, therefore, is very useful for batch cultures, but can also be beneficially used in fed-batch cultures or (fed-) perfusion cultures, such as those of the present invention.

Example 2

Feed Strategies for Improving Antibody Yields in PER.C6 Derived Sub-clones

Fed-batch processes aim at increasing product yields by increasing the viable cell concentration or prolonging the production period by feeding nutrient concentrates to replenish those that are consumed. We present here a feed strategy for improving the antibody yields of PER.C6® derived sub-clones. The feed strategy can be combined with a higher starting cell density to obtain a higher final cell density at the onset of the nutrient feed and a shorter overall production process.

A basic nutrient feed concentrate consisting of glucose, phosphate, glutamine and the 15 other amino acids was prepared based on the nutrient utilization profile of six duplicate batch cultures of clone 1 in shake-flask (see, e.g., FIG. 3). Similar utilization profiles were observed for clone 2, and, hence, it is expected that the feed strategy described below for clone 1 will also improve yields from other clones, thereby providing a more generic strategy for fed-batch or fed-perfusion cultures of E1-immortalized cells, preferably, retina cells, preferably, cells derived from PER.C6 cells. The concentrate is listed in Table 1. Optionally, calcium and three recombinant growth factors, LongR3 IGF-1, Long EGF and insulin were also added to the feed. At this point, the addition of calcium and the growth factors did not significantly influence the results that were obtained. Glycine appeared not essential for the feed, and was no longer added in later experiments. Insulin was purchased from Sigma, LongR3 IGF-1 and Long EGF were purchased from GroPep. All amino acids were purchased from Sigma. The timing and frequency of addition of the feed concentrates was varied. The time of the first addition was tested at 0, 1, and 2 days prior to nutrient exhaustion. Glucose and phosphate were used as indicators for the start of the feed. A series of bolus additions were made every two days, based on the predicted viable cell concentration. Usually, six feeds were provided. The concentrations of the added components as presented in Table 1 do not take into account the remaining component in the spent medium before the addition (i.e., the concentration of a component after addition into the culture medium will be higher than that provided in Table 1, because before the addition the culture medium will still contain some of this component, as additions, according to the invention, are done before the component is completely used up by the cells).

Figure 4:
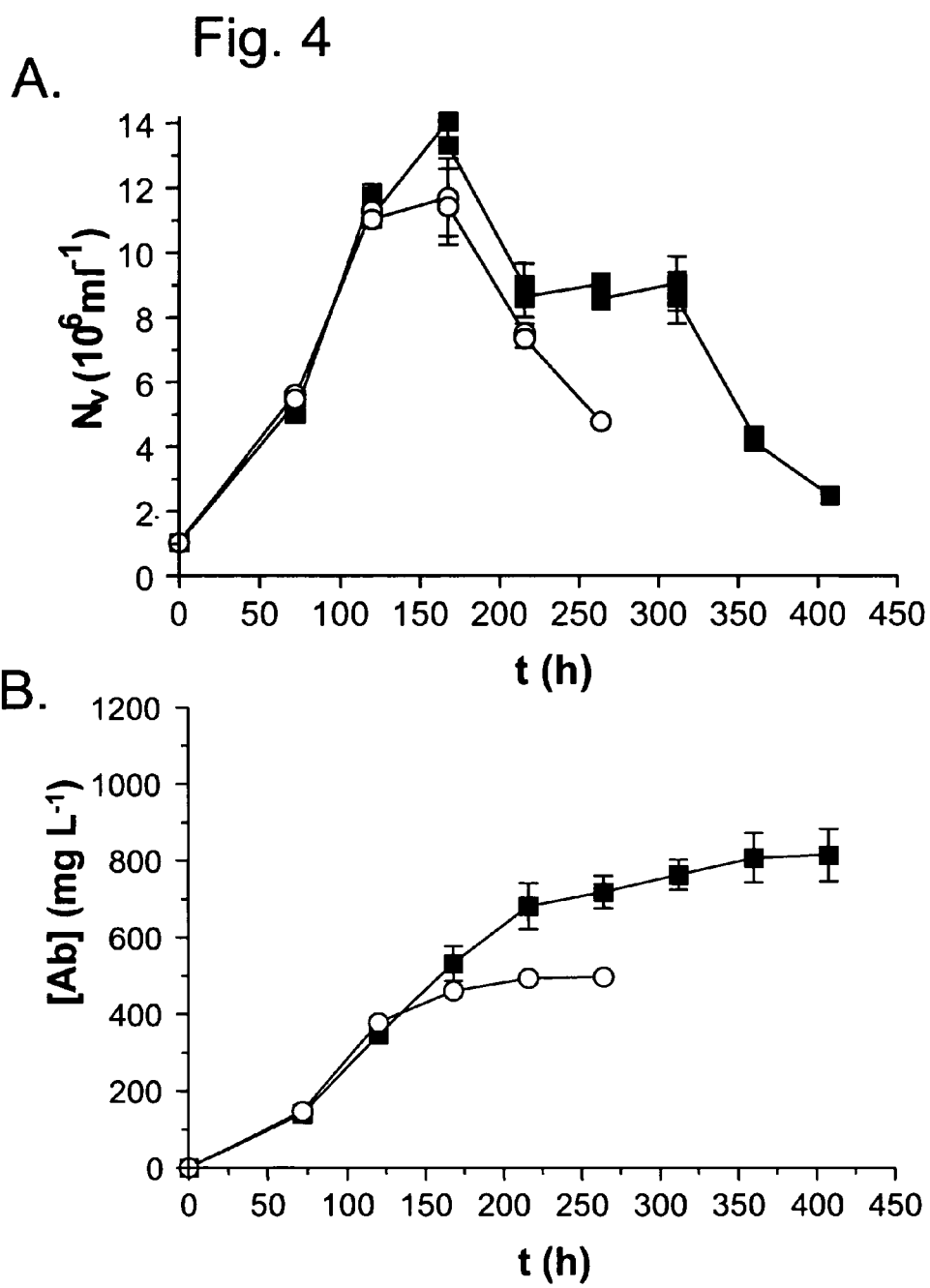
FIG. 4. Graph showing the effect of a feed component mix containing glucose, glutamine, amino acids, phosphate, calcium and growth factors on PER.C6 clone 1. A: viable cell numbers ($N_v$). B: antibody (Ab) concentration. Circles: batch. Squares: fed-batch.

FIG. 4 shows the effect of feeding the concentrate mix to a sub-clone of PER.C6® expressing a recombinant antibody (clone 1). Starting the feed at day 3 (two days prior to nutrient exhaustion and continuing every two days after this) resulted in a final antibody yield of approximately 800 mg L$^{-1}$, an increase of approximately 1.6-fold over the batch process, which gave 500 mg L$^{-1}$. Starting the feed at day 5 and continuing every two days after this) resulted in a similar increase in final antibody concentration.

Osmolality in the batch cultures (Example 1) decreased from 280 to 240 mOsm Kg$^{-1}$, while in the feed cultures, it increased, eventually rising to 300-310 mOsm Kg$^{-1}$.

Example 3

Achieving Viable Cell Numbers Above $30 \times 10^6$ Cells Per ml and Antibody Yields Above 500 mg L$^{-1}$ day$^{-1}$ Fed-batch processes may result in a build-up of toxic metabolites such as lactate and ammonia and an increase in medium osmolarity, which eventually limit the viable cell concentration and the length of the process, thus, impacting on product yields. A possible alternative to a fed-batch process is a perfusion process, where high cell concentrations can be maintained by a continual medium exchange and a cell bleed (removing a certain percentage of the cells population). A possible drawback with such a process is a relatively low product concentration due to the large volumes of medium that are required, the relatively low cell viability often encountered and the relatively high level of complexity to operate such a system. It is, therefore, only advantageous to operate perfusion processes if very high viable cell concentrations and/or specific productivities can be maintained.

We present here the attainment of a viable cell concentration above $30 \times 10^6$ ml$^{-1}$ and antibody yields of above 600 mg L$^{-1}$ 24 hours$^{-1}$ in shake flask cultures with one medium volume exchange per day.

Logarithmic cultures of antibody producing PER.C6® cells, cultured in shake flask with EXCELL™ 525 were transferred into shake flasks containing EXCELL™ VPRO at a starting cell number $1 \times 10^6$ cells/ml (other starting cell concentrations gave similar results). Medium replacement by centrifugation (one volume per day) was started at day 3-5. No cell bleed was operated. Samples for metabolite analysis, antibody quantification, and cell counts were taken every day and stored at −20° C.

FIG. 5 shows that a viable cell number of up to $50 \times 10^6$ ml$^{-1}$ and an antibody yield of 500-750 mg L$^{-1}$ 24 hours$^{-1}$ was maintained for at least five days without a cell bleed, for two independent antibody producing cell clones. Viability of the cells was around 80-90%. These high cell densities are approximately three-fold higher than is generally achievable with other cell lines like CHO and Sp2/0, and, hence, retina cells that are immortalized with adenovirus E1 sequences, such as PER.C6® cells, are very suitable for perfusion processes. A cell bleed will improve the length of the process, and, therefore, an optimized system may include one or more cell bleed steps.

Up to $50 \times 10^6$ cells per ml, with a viability of around 80-90%, could be maintained for at least five days with one complete medium change every two days. With this strategy, many of the nutrients became depleted on the second day. The medium is therefore, preferably, changed daily. In a perfusion process, this could translate into a change of about 1 to 3 volumes/day. This is near the typical range in a standard perfusion system, where the medium is changed at about 0.5 to 2 volumes/day. The somewhat higher values for the cells, according to the invention, are due to the very high cell concentrations with the cells of the invention in a perfusion system. When cell concentrations of more than $30 \times 10^6$ cells/ml according to the invention are preferred, the medium exchange should at least be 0.5 culture volumes/day, preferably, at least one culture volume/day. Failure to supply the nutrients (here via the culture medium) in sufficient concentration leads to cell death. The daily medium change results in higher viable cell densities (up to $50 \times 10^6$ cells/ml with daily medium change vs. $10 \times 10^6$ cells/ml without daily medium change, see FIGS. 1 and 4). Furthermore, with a daily medium exchange, the cells give similar product yields in one day as achieved in a batch process of 8 to 13 days.

Example 4

Feed Strategies for Further Improving Antibody Yields in PER.C6 Derived Sub-clones The provision of a balanced nutrient feed extends to components such as vitamins, trace elements and lipids. Concentrates (10× or 50×, both worked) of EXCELL® VPRO vitamins, inorganic salts, trace elements, growth factors, lipids and plant hydrolysates were obtained from JRH Biosciences and added together with the basic feed concentrate (minus calcium and growth factors) described in Example 2. The EXCELL® VPRO concentrates were added to give a final concentration of 0.25×.

Figure 6:
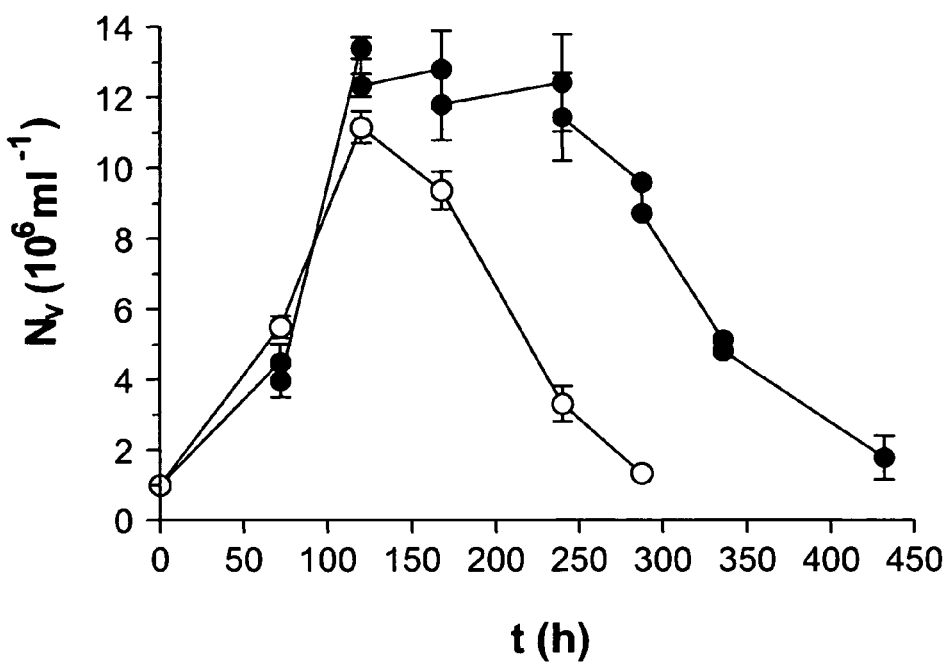
FIG. 6. Result of modified feed (example 4) for clone 1. A: viable cell numbers ($N_v$). B: antibody (Ab) concentration. Open circles: batch. Closed circles: fed-batch.
Figure 6:
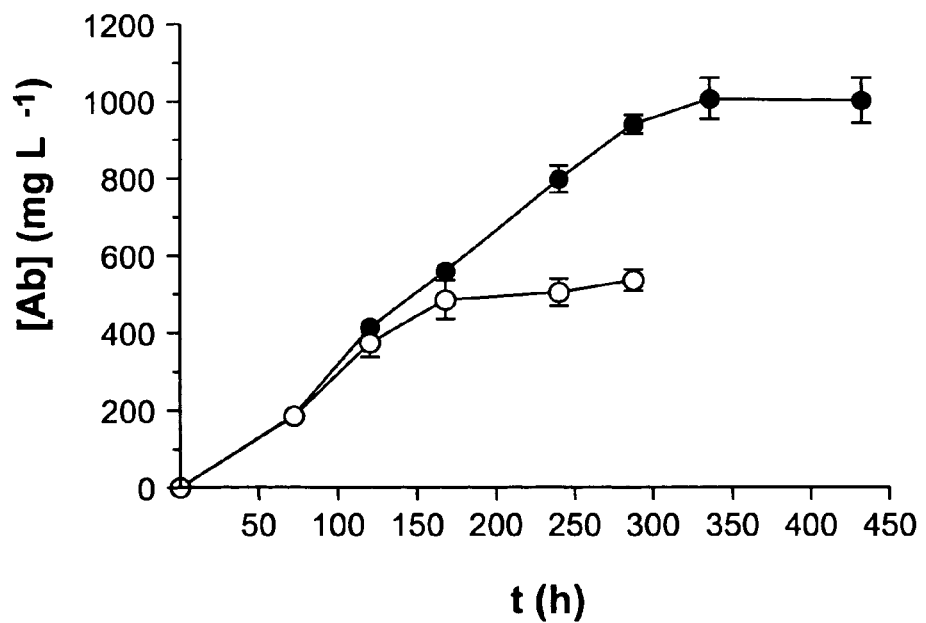

FIG. 6 shows the results of this modified feed on the growth (FIG. 6A) and antibody yields (FIG. 6B) of clone 1 in shake-flask versus a batch control. The results were obtained by starting the feed at day 3 (48 hours prior to nutrient depletion). Starting the feed at day 5 (day of nutrient depletion) gave similar results. The viable cell number was maintained for significantly longer than the batch control and antibody yields increased 2.0-fold from 0.5 g L$^{-1}$ in the batch to 1.0 g L$^{-1}$ in the fed-batch process.

Spent medium analysis of these feed experiments identified a change in the cell specific rates of utilization of some of the amino acids, which appeared to be due to the addition of the VPRO concentrates. The amino acid concentrate listed in Example 2 was, therefore, modified as shown in Table 2. The feed was started 48 hours prior to nutrient depletion and additions were made every two days. Usually, six feeds were provided. Again, the concentrations of the added components as presented in Table 2 do not take into account the remaining component in the spent medium before the addition.

For the first feed addition, increased concentrations of glutamine and serine were used as compared to the subsequent feeds (see Table 2). Phosphate and glucose were used as markers to determine the start of the feed. Clones 1 and 2 were used in this experiment.

Experiments were carried out in shake-flask and bioreactor. Shake flask experiments were carried out as described. Bioreactor experiments were initiated by inoculating a 3L bioreactor (Applikon, 2L working volume) with cells from a logarithmic pre-culture grown in shake flask. The pre-culture and bioreactor experiments were performed in EXCELL® VPRO. The split ratio for inoculation into the bioreactor was at least 1:6, and the seeding cell concentration was about $0.3 \times 10^6$ cells/ml.

Results

Figure 7:
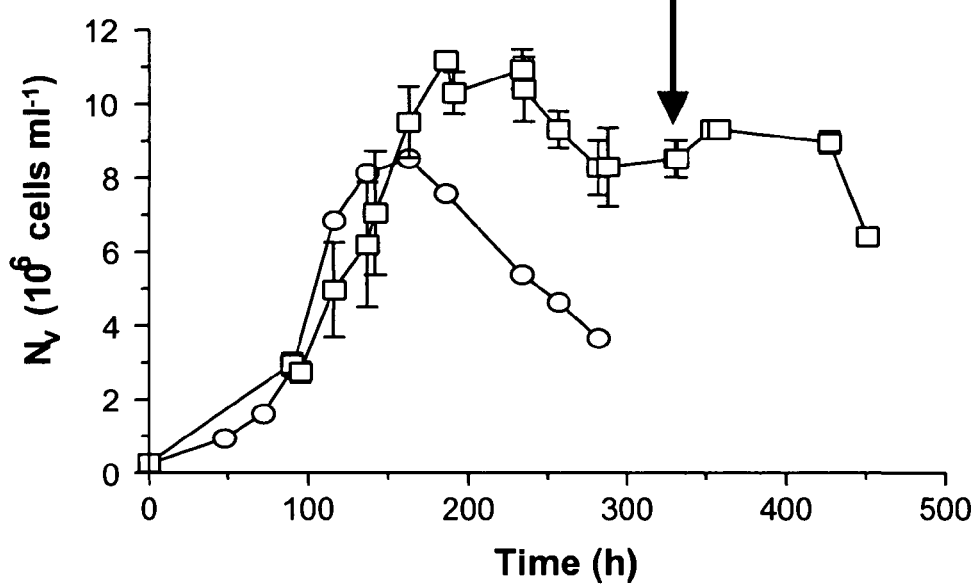
FIG. 7. Result of further improved modified feed with different first and subsequent feed additions (Example 4, Table 2) for clone 1. A: viable cell numbers ($N_v$). B: antibody (Ab) concentration. Circles: batch. Squares: fed-batch. Arrows: last feed.
Figure 7:
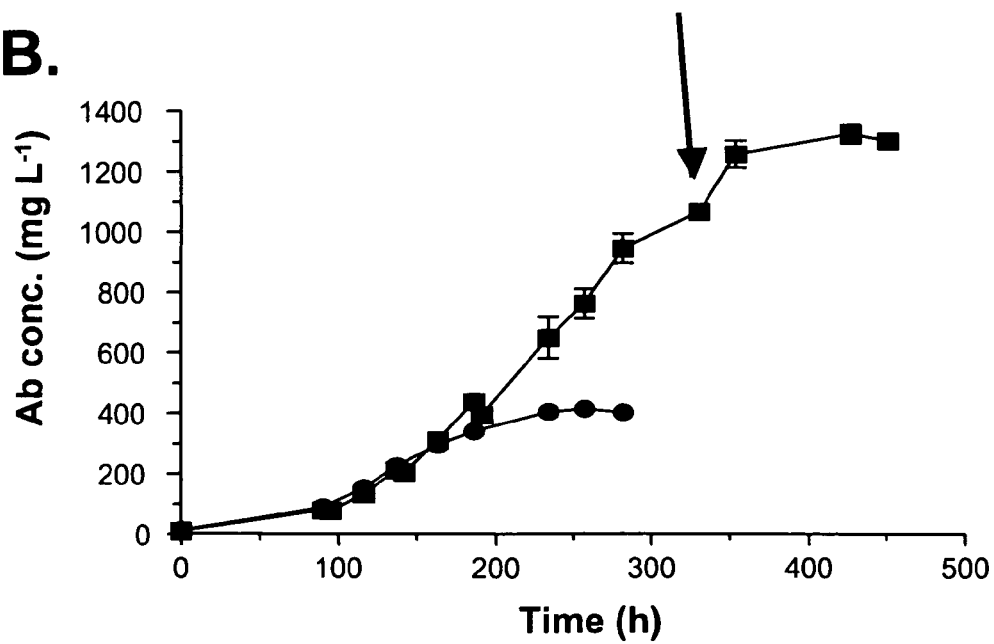

FIG. 7 shows the results of the modified feed on clone 1 in bioreactor versus a batch control. The maximum viable cell number reached $10-12 \times 10^6$ ml$^{-1}$ and viable cell numbers were maintained between 8 and $10 \times 10^6$ cells ml$^{-1}$ until the end of the culture at day 19 (FIG. 7A). Antibody yields increased three-fold from 0.4 g L$^{-1}$ in the batch to 1.3 g L$^{-1}$ in the fed-batch process (FIG. 7B).

Osmolality and ammonia reached 430 mOsm Kg$^{-1}$ and 16 mmoles L$^{-1}$, respectively, in these feed cultures, levels that have been reported as having negative effects on culture performance and product quality. It may, therefore, be that the decrease in viable cell numbers observed towards the end of the process was due, at least in part, to these factors.

Figure 8:
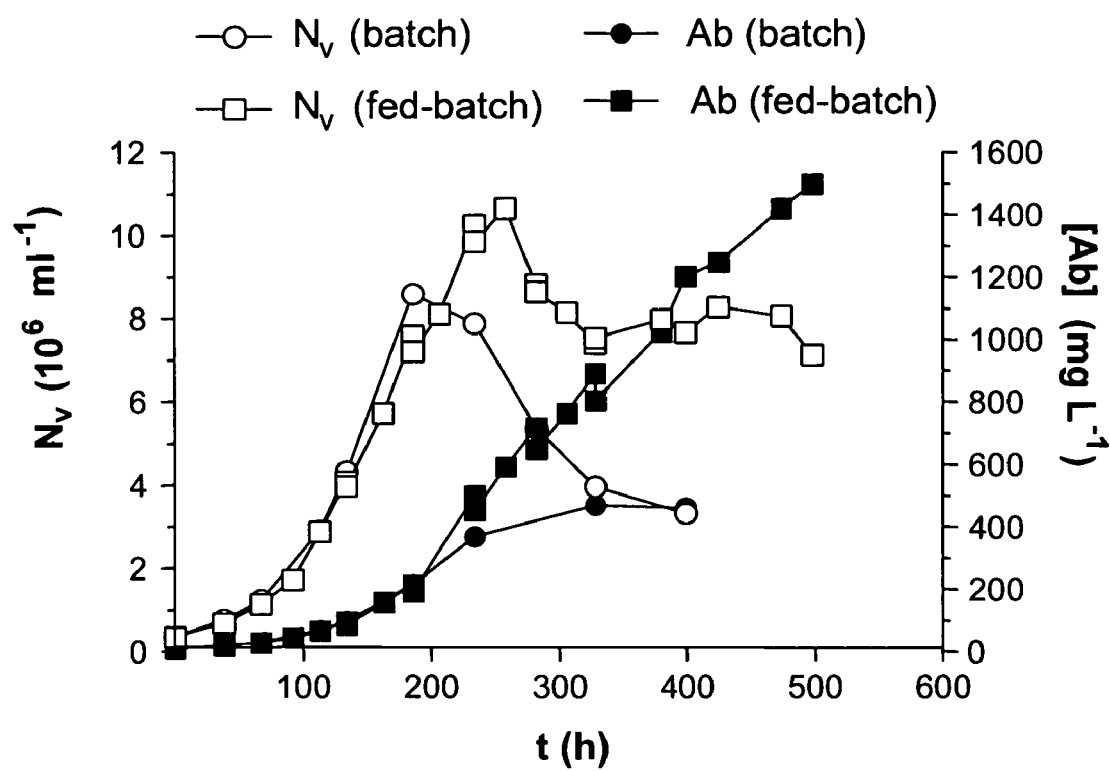
FIG. 8. Result of further improved modified feed with different first and subsequent feed additions (Example 4, Table 2) for clone 2. $N_v$: viable cell number. Ab: antibody concentration.

FIG. 8 shows the results of the feed strategy on clone 2 in 2L bioreactors. Maximum viable cell numbers reached $10\text{-}11\times10^6$ ml$^{-1}$ and $7\text{-}9\times10^6$ ml$^{-1}$ were maintained until the end of the culture at 19 days. Antibody yields were increased three-fold from 0.5 g L$^{-1}$ to 1.5 g L$^{-1}$.

Figure 10:
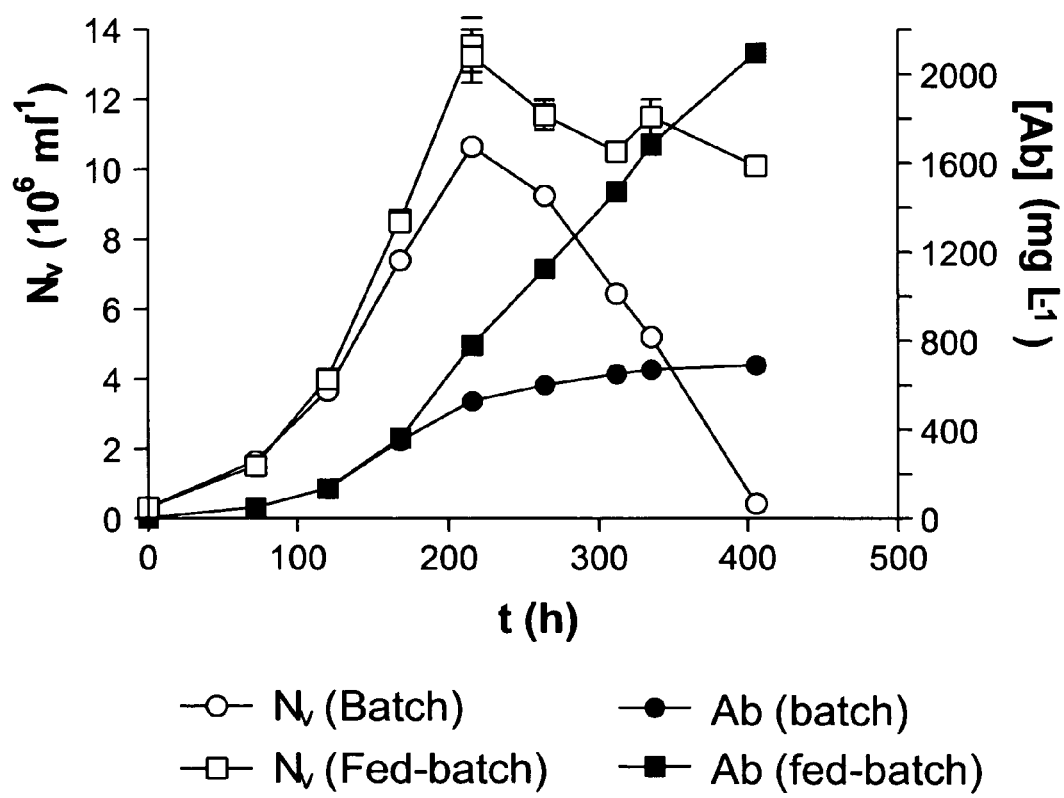
FIG. 10. Result of further improved modified feed with different first and subsequent feed additions (Example 4, Table 2) for clone 3. $N_v$: viable cell numbers. Ab: antibody concentration.

A third clone expressing another, again unrelated, antibody was subjected to the same batch process and the fed-batch process with the same feed strategy. FIG. 10 shows the results of the feed strategy on this clone 3 in shake flask. Maximum viable cell numbers reached $14\times10^6$ ml$^{-1}$ and $10\text{-}12\times10^6$ ml$^{-1}$ were maintained until the end of the culture on day 17. Antibody yields were increased three-fold from 0.7 g L$^{-1}$ to 2.1 g L$^{-1}$.

The feed strategy, therefore, improves the yield for different clones that each express a different antibody, indicating that the process, according to the invention, is generically applicable.

It is, therefore, an aspect of the invention to provide a process comprising the feed strategy, according to the invention, wherein the yield of a produced protein is increased at least 1.5×, preferably, at least 2×, more preferably, at least 2.5×, still more preferably, at least 3× over the yield in the batch process.

The specific productivity ($q_{Ab}$) of the cells used in the present invention was approximately between 12 to 18 pg antibody/cell/day. In some instances the $q_{Ab}$ was around 10 pg antibody/cell/day, and in other instances values up to about 25 pg antibody/cell/day were observed with the cells and methods of the present invention. In the batch cultures, this decreased significantly before maximum cell numbers were reached, coinciding with depletion of nutrients, which was approximately after seven days, whereas in fed-batch cultures this specific productivity was kept at this level until two to three days after the last feed addition, which amounted to around 16 to 18 days, according to a process of the invention.

Product Quality

In the experiments described above, product quality was checked by various methods, including iso-electric focusing, SDS-PAGE, MALDI-TOF mass spectrometry and HPAEC-PAD. In all cases, the produced antibody basically showed a human-type glycosylation and the structural integrity of the produced antibodies was very good, irrespective of the process used, and very similar to that reported in (Jones et al., 2003), where both cell numbers and product yields were lower. Therefore, the increased yields obtainable by processes of the invention were not obtained at the cost of a significant decrease in product quality.

Protein A purified IgG produced from batch and fed-batch cultures was analyzed by MALDI-MS. Material produced by PER.C6 cells from batch cultures showed a galactosylation profile similar to that shown by IgG purified from human serum and no hybrid or high mannose structures were identified in either batch or fed-batch produced material. The average percentage of glycans terminating in 0, 1, and 2 galactose residues (G0:G1:G2) from all the batch cultures tested was 29, 54, and 17%, respectively. This can be compared to CHO and hybridoma produced antibody, which is often predominantly in the G0 form. For example, Hills et al. (1999) reported a galactosylation profile (G0: G1:G2) for an antibody produced in NS0 and CHO cells.

Figure 9:
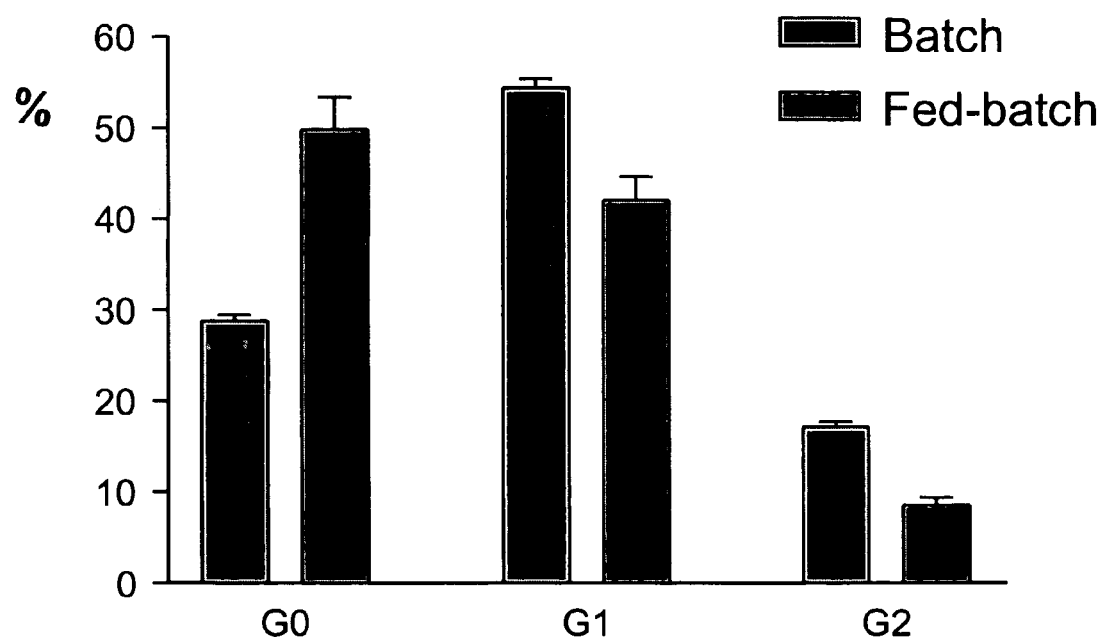
FIG. 9. Galactosylation levels of IgG produced according to processes according to invention.

Antibody produced in the fed-batch process showed a reduced level of galactosylation compared to the batch (FIG. 9). The percentage of G0 glycoforms increased from 29 to 49%, while the G1 and G2 glycoforms decreased from 54% and 17% to 42% and 9%, respectively. This decrease in galactosylation was probably due to the high (up to 16 mM) ammonia concentrations at the end of the fed-batch cultures. However, the level of galactosylation in the antibody produced by the fed-batch process in PER.C6 cells was still higher than typically seen in batch-produced antibodies from CHO, for example, (Hills et al., 1999). Isoelectric focusing (IEF) and SDS-PAGE revealed no significant differences between the material produced by batch or fed-batch cultures (data not shown) and in all cases, aggregation was below 3%.

Despite relatively low $Y_{amm/gln}$ values, the high viable cell concentrations resulted in a supply of glutamine in the feed such that the ammonia accumulated up to 16 mmoles L$^{-1}$. While this did not result in a drop in the viable cell concentration, batch cultures initiated in the presence of NH$_4$Cl showed that concentrations above 9 mmole L$^{-1}$ negatively affected growth rates and maximum cell concentrations. Furthermore, glycosylation was also somewhat affected (see FIG. 9). It may, therefore, be beneficial to reduce ammonia accumulation, e.g., according to a method described below.

Two areas for attention in the process described so far are the high levels of ammonia and osmolality. A large contributor to the increase in osmolality came from the VPRO (medium) concentrates. An approach to reduce this osmolality is, therefore, to identify which of the medium component groups (vitamins, trace elements, inorganic salts, growth factors etc.) are important to culture performance and remove those that are not important. This should benefit the process, not only by reducing the osmolality of the feed, but also by removing any potentially deleterious components and by allowing the optimization of addition of the most important components. It would also reduce the cost of the feed.

Reduction in ammonia accumulation may be achieved by more strictly controlling glutamine addition. This can be done based on the calculations of the specific consumption and cell numbers, as described supra. This can be achieved by continuously pumping in glutamine at an appropriate rate, matched to the viable cell concentration and the cell specific rate of utilization, so that residual glutamine concentrations in the medium are maintained at a constant low level, such as between 0.2 and 1.5 mM, preferably, between 0.5 and 1.0 mM. Another approach that may be possible for the cells, according to the invention, is the removal of glutamine from the feed when the ammonia concentration reaches a certain point, e.g., in one or more of the feeds, subsequent to the first feed, so that the cells are forced to switch to glutamine synthesis using ammonia and glutamate and the glutamine synthetase pathway. This approach is not generally possible for cell types such as BHK and CHO, as glutamine depletion often results in rapid and widespread cell death and transfer to glutamine-free conditions often requires a period of adaptation. However, in batch cultures of the cells, according to the present invention, the viable cell concentration continued to increase for two days after the depletion of glutamine and culture viability was not significantly affected, suggesting that there may be sufficient flux through the glutamine synthetase pathway at least to maintain the culture.

Spent medium analysis of the most optimized fed-batch culture (examples in FIGS. 7, 8) showed that only cystine was depleted during the process. A further modification of the amino acid feed, according to the invention, is, therefore, an increase in the cystine concentration, e.g., to 0.3 to 0.35 mmoles/l or even up to 0.6 mmoles/l for every $10 \times 10^6$ cells/ml.

Example 5

Improved (Fed-)Batch Process

Feed concentrates developed for fed-batch processes may also be used to supplement culture media for use in an improved batch process. Supplementing a culture medium with at least one of the feed additions from a fed-batch process has been shown by others to improve batch yields. A similar approach of supplementing culture media with feed concentrates may also be used to reduce the number of feed additions during a fed-batch process, thereby simplifying the process, as also shown by others.

The present invention discloses feed strategies for cells that have been immortalized by adenovirus E1 sequences, such as PER.C6 cells. It is shown herein which components become limiting in a fed-batch process, and the amounts of, as well as the ratio between, the components that can be added to improve yields in a fed-batch process are disclosed herein. This information is used, in this example, to provide an improved batch process. It is assumed that such a culture will contain about $10 \times 10^6$ cells/ml, as this is around the number of cells that has been observed in the batch and fed-batch cultures of the invention. In the fed-batch experiments, six feeds were added, with concentrations of the components as in Tables 1 or 2. The addition of 10% to 60% of the total (i.e., the total of all six feeds together) feed, preferably, 20% to 40% of the total feed, results in an improved batch process, because the nutrients will become depleted later during the culture, and, hence, the yields will go up because of prolonged productivity compared to the straight batch process disclosed above, where no additions are made to the culture medium. The components can be added directly to the culture medium at any stage prior to depletion of nutrients from the medium, but are, preferably, added prior to start of the culture so that no other additions have to be made during the process (improved batch process), which makes the process very simple. Of course, this may be combined with extra additions of certain components later during the process (fed-batch process), in which case less additions have to be made to make the process than in the fed-batch process disclosed above, thereby providing a simpler fed-batch process. It is, therefore, another embodiment of the invention to provide a method for producing a product in cells immortalized by adenovirus E1 sequences, wherein the cells are cultured in a culture medium, characterized in that the following components are added to the culture medium in the following amounts: glucose (3.6-21.6 mmoles/l, preferably, 7.2-14.4 mmoles/l), glutamine (6.8-40.9 mmoles/l, preferably, 13.6-27.2 mmoles/l), leucine (0.40-2.4 mmoles/l, preferably, 0.79-1.6 mmoles/l), serine (2.31-13.9 mmoles/l, preferably, 4.62-9.24 mmoles/l), isoleucine (0.3-1.8 mmoles/l, preferably, 0.6-1.2 mmoles/l), arginine (0.28-1.66 mmoles/l, preferably, 0.55-1.10 mmoles/l), methionine (0.14-0.83 mmoles/l, preferably, 0.28-0.55 mmoles/l), cystine (0.15-0.9 mmoles/l, preferably, 0.3-0.6 mmoles/l), valine (0.27-1.62 mmoles/l, preferably, 0.54-1.08 mmoles/l), lysine (0.26-1.58 mmoles/l, preferably, 0.53-1.06 mmoles/l), threonine (0.18-1.08 mmoles/l, preferably, 0.36-0.72 mmoles/l), asparagine (0.06-0.36 mmoles/l, preferably, 0.12-0.24 mmoles/l), tyrosine (0.078-0.47 mmoles/l, preferably, 0.16-0.31 mmoles/l), histidine (0.06-0.36 mmoles/l, preferably, 0.12-0.24 mmoles/l), phenylalanine (0.012-0.072 mmoles/l, preferably, 0.024-0.048 mmoles/l), tryptophan (0.036-0.22 mmoles/l, preferably, 0.072-0.14 mmoles/l) and phosphate (0.45-2.7 mmoles/l, preferably, 0.9-1.8 mmoles/l). The amounts between brackets are 10% to 60%, preferably, 20% to 40%, of the amounts of 6× the feeds of Table 2. Preferably, also culture medium concentrate (10×, 50×, or other suitable concentrates can be used) is added to an end concentration of between 0.15×-0.9×, preferably, between 0.3×-0.6×. Preferably, the culture medium in these embodiments is ExCell VPRO medium. An amount of 0.5, 1, 1.5, 2, 2.5, 3, 3.5 or 4 single feeds (a single feed being an amount as disclosed in Table 1 or 2) is added to culture medium, and simple batch processes for culturing the cells at around $10 \times 10^6$ cells/ml and producing product (e.g., antibody), according to the invention, are performed with the, thus, fortified media, to determine the optimum amount of component additions. Improved batch processes giving the highest product yields are expected when about 20% to 40% of the total feed of a fed-batch process, according to the invention, are provided to the culture medium prior to culturing somewhere between 1 to 2.5 single feeds. Of course, more fine-tuning of the amount is possible once a beneficial range of added components is established by these experiments. Of course, when the cell numbers are different, the component addition can again be adapted. For instance, if the cells are cultured at a density of only $5 \times 10^6$ cells/ml, addition of an amount of only half the amount above would be required, as is clear to the person skilled in the art.

TABLE 1

| Components | Final Concentration (after addition) (per $10 \times 10^6$ cells/ml) (mmoles $L^{-1}$) |
|---|---|
| Glucose | 6.00 |
| Glutamine | 1.75 |
| Leucine | 0.60 |
| Serine | 0.55 |
| Isoleucine | 0.45 |
| Arginine | 0.42 |
| Methionine | 0.23 |
| Cystine | 0.14 |
| Valine | 0.45 |
| Lysine | 0.40 |
| Threonine | 0.33 |
| Glycine | 0.33 |
| Asparagine | 0.15 |
| Tyrosine | 0.14 |
| Histidine | 0.11 |
| Penylalanine | 0.10 |
| Tryptophan | 0.02 |
| Phosphate | 0.70 |
| Calcium | 0.02* |
| LongR3 IGF-1 | 50 ug/L* |
| Long EGF | 50 ug/L* |
| Insulin | 20 ug/L* |

*optionally present

TABLE 2

| Components | Final Concentration (after addition) (per $10 \times 10^6$ cells/ml) (mmoles $L^{-1}$) | |
|---|---|---|
| | First Feed | Subsequent Feeds |
| Glucose | 6.00 | 6.00 |
| Glutamine | 2.60 | 1.75 |

TABLE 2-continued

| Components | Final Concentration (after addition) (per 10 × 10⁶ cells/ml) (mmoles L⁻¹) | |
|---|---|---|
| | First Feed | Subsequent Feeds |
| Leucine | 0.66 | 0.66 |
| Serine | 1.10 | 0.55 |
| Isoleucine | 0.50 | 0.50 |
| Arginine | 0.46 | 0.46 |
| Methionine | 0.23 | 0.23 |
| Cystine | 0.25 | 0.23 |
| Valine | 0.45 | 0.45 |
| Lysine | 0.44 | 0.44 |
| Threonine | 0.30 | 0.30 |
| Asparagine | 0.10 | 0.10 |
| Tyrosine | 0.13 | 0.13 |
| Histidine | 0.10 | 0.10 |
| Penylalanine | 0.02 | 0.02 |
| Tryptophan | 0.06 | 0.06 |
| Phosphate | 0.75 | 0.75 |
| 10X VPRO Concentrate | 0.25X | 0.25X |

REFERENCES

Boel E., S. Verlaan, M. J. Poppelier, N. A. Westerdaal, J. A. Van Strijp, and T. Logtenberg (2000). Functional human monoclonal antibodies of all isotypes constructed from phage display library-derived single-chain Fv antibody fragments. *J. Immunol. Methods* 239:153-66.

Hills A. E., A. K. Patel, P. N. Boyd and D. C. James (1999). Control of therapeutic antibody glycosylation. In: A. Bernard, B. Griffiths, W. Noe and F. Wurm (eds), *Animal Cell Technology: Products from Cells, Cells as Products*, 255-257. Kluwer Academic Press, Dordrecht, The Netherlands.

Huls G. A., I. A. F. M. Heijnen, M. E. Cuomo, J. C. Koningsberger, L. Wiegman, E. Boel, A-R van der Vuurst-de Vries, S. A. J. Loyson, W. Helfrich, G. P. van Berge Henegouwen, M. van Meijer, J. de Kruif, and T. Logtenberg (1999). A recombinant, fully human monoclonal antibody with antitumor activity constructed from phage-displayed antibody fragments. *Nat. Biotechnol.* 17:276-281.

Jones D., N. Kroos, R. Anema, B. Van Montfort, A. Vooys, S. Van Der Kraats, E. Van Der Helm, S. Smits, J. Schouten, K. Brouwer, F. Lagerwerf, P. Van Berkel, D-J Opstelten, T. Logtenberg, and A. Bout (2003). High-level expression of recombinant IgG in the human cell line PER.C6. *Biotechnol. Prog.* 19:163-168.

Portner R., A. Bohmann, I. Ludemann and H. Markl (1994). Estimation of specific glucose uptake rates in cultures of hybridoma cells. *J. Biotechnol.* 34:237-246.

Sauer P. W., J. E. Burky, M. C. Wesson, H. D. Sternard and L. Qu (2000). A high yielding, generic process fed batch cell culture process for production of recombinant antibodies. *Biotechnol. Bioeng.* 67:585-597.

Tanase T., Y. Ikeda, K. Iwama, A. Hashimoto, T. Kataoka, Y. Tokushima and T. Kobayashi (1997). Comparison of micro-filtration hollow fiber bioreactors for mammalian cell culture. *J Ferm. Ioeng.* 83:499-501.

Xie L., W. Pilbrough, C. Metallo, T. Zhong, L. Pikus, J. Leung, Auniṇš and W. Zhou (2002). Serum-free suspension cultivation of PER.C6® cells and recombinant adenovirus production under different pH conditions. *Biotechnol. and Bioengin.* 80:569-579.

Weidemann R., A. Ludwig and G. Kretzmer (1994). Low temperature cultivation—A step towards process optimization. *Cytotechnology* 15:111-116.

Wohlpart D., D. Kirwan and J. Gainer (1990). Effects of cell density and glucose and glutamine levels on the respiration rates of hybridoma cells. *Biotechnol. Bioeng.* 36:630-635.

Yallop C. A. and I. Svendsen (2001). The effects of G418 on the growth and metabolism of recombinant mammalian cell lines. *Cytotechnology* 35:101-114.

What is claimed is:

1. A method for culturing cells, said cells being human embryonic retina (HER) cells immortalized by adenovirus E1 sequences and able to grow in suspension, the method comprising the steps of:
   a) determining at least once during the culturing of the cells the concentration of at least one medium component selected from the group consisting of glucose, glutamine, phosphate, leucine, serine, isoleucine, arginine, methionine and cystine, and
   b) adding components to the medium during the culturing of the cells at or prior to the depletion of at least one of the components of which the concentration was determined in step a), wherein the components added at least comprise glucose, glutamine, phosphate, leucine, serine, isoleucine, arginine, methionine and cystine, wherein components in step b) are added to an end concentration in mmoles/l of freshly added component per 10×10⁶ cells/ml of between 4.0 and 8.0 for glucose, 0.47 and 0.93 for phosphate, 0.44 and 0.88 for leucine, 0.37 and 1.47 for serine, 0.33 and 0.67 for isoleucine, 0.31 and 0.61 for arginine, 0.15 and 0.31 for methionine, and 0.1 and 0.6 for cystine.

2. The method according to claim 1, wherein in step a) the concentration is determined from at least two of said medium components.

3. The method according to claim 1, wherein the components added in step b) further comprise one or more of valine, lysine, threonine, glycine, asparagine, tyrosine, histidine, phenylalanine, tryptophan, phosphate, calcium, LongR3 IGF-1, Long EGF and insulin.

4. The method according to claim 1, wherein in step b) glutamine is further added to an end concentration of 1.17 and 3.47 mmoles/l of freshly added glutamine per 10×10⁶ cells/ml.

5. The method according to claim 4, wherein the components in step b) are added more than one time, and further characterized in that, as a result of the first addition, the end concentration of freshly added glutamine is higher than as a result of a subsequent addition.

6. The method according to claim 1, wherein glutamine is further added continuously such that the residual concentration of glutamine in the medium is maintained between 0.2 and 1.5 mM or between 0.5 and 1.0 mM.

7. The method according to claim 1, wherein in step b) the following components are further added to an end concentration in mmoles/l of freshly added component per 10×10⁶ cells/ml of between 0.3 and 0.6 for valine, 0.29 and 0.59 for lysine, 0.2 and 0.4 for threonine.

8. The method according to claim 7, wherein in step b) the following components are further added to an end concentration in mmoles/liter of freshly added component per 10×10⁶ cells/ml of between 0.067 and 0.13 for asparagine, 0.087 and 0.17 for tyrosine, 0.067 and 0.13 for histidine, 0.013 and 0.027 for phenylalanine, and 0.04 and 0.08 for tryptophan.

9. The method according to claim 1, wherein the addition of the components in step b) is performed at between 48 hours and just prior to depletion of at least one of the medium components the concentration of which was determined in the previous step.

10. The method according to claim 1, wherein said steps are repeated at least once.

11. The method according to claim 1, wherein said cells are PER.C6 cells as deposited under ECACC No. 96022940.

12. The method according to claim 1, wherein the cells are grown to a cell density of at least $9 \times 10^6$ per ml.

13. The method according to claim 1, wherein the cells produce a product that is harvested.

14. The method according to claim 13, wherein said product is a recombinant protein.

15. The method according to claim 14, wherein said recombinant protein is an immunoglobulin that is secreted into the culture medium to a level of at least 500 mg per liter.

16. The method according to claim 15, wherein said recombinant protein is an immunoglobulin that is secreted into the culture medium to a level of at least 1000 mg per liter.

17. The method according to claim 1, wherein the cells are in suspension during culturing.

18. A method for producing a product in HER cells immortalized by adenovirus E1 sequences, said cells being in a culture medium, wherein said product is chosen from the group consisting of a recombinant protein, a virus, and a recombinant adenovirus with a deletion in the E1 region, the method comprising the step of adding at least glutamine, glucose, phosphate, leucine, serine, isoleucine, arginine, methionine and cystine to the cluture medium to an end concentration in mmoles/liter of freshly added component per $10 \times 10^6$ cells/ml of between 1.01 and 3.46 for glutamine, 4.0 and 8.0 for glucose, 0.47 and 0.93 for phosphate, 0.44 and 0.88 for leucine, 0.37 and 1.47 for serine, 0.33 and 0.67 for isoleucine, 0.31 and 0.61 for arginine, 0.15 and 0.31 for methionine, and 0.1 and 0.6 for cystine.

19. The method according to claim 18, further characterized in that said cells reach a cell concentration of at least $20 \times 10^6$ or at least $30 \times 10^6$ viable cells/ml at least part of the time in said process.

20. A method for producing a product in HER cells immortalized by adenovirus E1 sequences, wherein said cells are cultured in a culture medium, comprising the step of the following components to the culture medium in the following amounts per liter:
3.6-21.6 mmoles glucose,
6.8-40.9 mmoles glutamine,
0.40-2.4 mmoles leucine,
2.31-13.9 mmoles serine,
0.3-1.8 mmoles isoleucine,
0.28-1.66 mmoles arginine,
0.14-0.83 mmoles methionine,
0.15-0.9 mmoles cystine,
0.27-1.62 mmoles valine,
0.26-1.58 mmoles lysine,
.18-1.08 mmoles threonine,
0.06-0.36 mmoles asparagine,
0.078-0.47 mmoles tyrosine,
0.06-0.36 mmoles histidine,
0.012-0.072 mmoles phenylalanine,
0.036-0.22 mmoles tryptophan, and 0.45-2.7 mmoles phosphate.

21. The method according to claim 20, wherein the amounts of the components added to the culture medium per liter are: 7.2-14.4 mmoles glucose, 13.6-27.2 mmoles glutamine, 0.79-1.6 mmoles leucine, 4.62-9.24 mmoles serine, 0.6-1.2 mmoles isoleucine, 0.55-1.10 mmoles arginine, 0.28-0.55 mmoles methionine, 0.3-0.6 mmoles cystine, 0.54-1.08 mmoles valine, 0.53-1.06 mmoles lysine, 0.3-0.72 mmoles threonine, 0.12-0.24 mmoles asparagine, 0.16-0.31 mmoles tyrosine, 0.12-0.24 mmoles histidine, 0.024-0.048 mmoles phenylalanine, 0.072-0.14 mmoles tryptophan and 0.9-1.8 mmoles phosphate.

22. The method according to claim 20, further comprising adding culture medium concentrate is to an end concentration of between 0.15×-0.9×.

23. The method according to claim 20, wherein said components are added to the culture medium prior to culturing the cells.

24. The method according to claim 20, further comprising adding culture medium concentrate to an end concentration of between 0.3×-0.6×.

* * * * *

UNITED STATES PATENT AND TRADEMARK OFFICE
CERTIFICATE OF CORRECTION

PATENT NO. : 7,291,484 B2
APPLICATION NO. : 11/259245
DATED : November 6, 2007
INVENTOR(S) : Christopher A. Yallop Page 1 of 1

It is certified that error appears in the above-identified patent and that said Letters Patent is hereby corrected as shown below:

On the title page:
In ITEM (56) References Cited
  OTHER PUBLICATIONS
Page 2, 2nd column, 4th line of the
  3rd entry (line 10), change "tot he" to --to the--
Page 2, 2nd column, 7th line of the
  3rd entry (line 13), change "715-725," to --718-725,--
Page 3, 1st column, 1st line of the
  16th entry (line 57), change "overian" to --ovarian--
Page 3, 2nd column, 2nd line of the
  5th entry (line 11), change "Phannaceuticals" to --Pharmaceuticals--
Page 3, 2nd column, 3rd line of the
  17th entry (line 48), change "Expression" to --Expressed--

Signed and Sealed this
Ninth Day of April, 2013

Teresa Stanek Rea
*Acting Director of the United States Patent and Trademark Office*